United States Patent
Li et al.

(10) Patent No.: US 10,261,080 B2
(45) Date of Patent: Apr. 16, 2019

(54) OPTICAL DETECTION SYSTEM FOR FLOW CYTOMETER, FLOW CYTOMETER SYSTEM AND METHODS OF USE

(71) Applicant: ACEA Biosciences, Inc., San Diego, CA (US)

(72) Inventors: Nan Li, San Diego, CA (US); Lingbo Kong, San Diego, CA (US); Jian Wu, Hangzhou (CN); Ting Cheng, Hangzhou (CN); Yangde Qin, Hangzhou (CN); Xiaobo Wang, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 0 days.

(21) Appl. No.: 15/650,896

(22) Filed: Jul. 15, 2017

(65) Prior Publication Data

US 2017/0315122 A1     Nov. 2, 2017

Related U.S. Application Data

(60) Continuation-in-part of application No. 15/416,976, filed on Jan. 26, 2017, which is a division of
(Continued)

(51) Int. Cl.
| | |
|---|---|
| *G01N 33/569* | (2006.01) |
| *G01N 15/14* | (2006.01) |
| *G01N 15/10* | (2006.01) |

(52) U.S. Cl.
CPC ... *G01N 33/56972* (2013.01); *G01N 15/1434* (2013.01); *G01N 15/1459* (2013.01);
(Continued)

(58) Field of Classification Search
CPC .......... G01N 15/1434; G01N 15/1459; G01N 2015/1006; G01N 2015/1402;
(Continued)

(56) References Cited

U.S. PATENT DOCUMENTS

| | | | |
|---|---|---|---|
| 4,482,994 | A | 11/1984 | Ishikawa |
| 4,573,796 | A | 3/1986 | Martin et al. |

(Continued)

FOREIGN PATENT DOCUMENTS

| | | |
|---|---|---|
| CN | 102087198 | 6/2011 |
| CN | 102334021 A | 1/2012 |

(Continued)

OTHER PUBLICATIONS

PCT/US2014/066429 International Search Report and Written Opinion dated Mar. 23, 2015.
(Continued)

*Primary Examiner* — Tri T Ton
(74) *Attorney, Agent, or Firm* — Wagenknecht IP Law Group PC

(57) ABSTRACT

An optical engine its use in a bench top flow cytometer, the optical engine having a set of lasers, each focused horizontally along an x-axis to a same horizontal position and vertically along a y-axis to a different vertical position along a same excitation plane of a flow cell, a set of optics that separate fluorescence of a same wavelength range into different locations in a focal plane of collection optics according to the different lasers by which the fluorescent light is excited; and a detector that selectively detects light from the different locations thereby distinguishing between fluorescence emitted within the same wavelength range as excited by the different lasers.

46 Claims, 14 Drawing Sheets

Related U.S. Application Data application No. 14/547,963, filed on Nov. 19, 2014, now Pat. No. 9,575,063.

(60) Provisional application No. 61/906,367, filed on Nov. 19, 2013, provisional application No. 61/994,980, filed on May 18, 2014, provisional application No. 62/363,032, filed on Jul. 15, 2016.

(52) U.S. Cl.
CPC ........... *G01N 2015/1006* (2013.01); *G01N 2015/1402* (2013.01); *G01N 2015/1438* (2013.01); *G01N 2015/1477* (2013.01)

(58) Field of Classification Search
CPC ... G01N 2015/1438; G01N 2015/1477; G01N 33/56972
USPC .................................................. 356/335–343
See application file for complete search history.

(56) References Cited

U.S. PATENT DOCUMENTS

| | | | |
|---|---|---|---|
| 4,707,064 A | 11/1987 | Dobrowolski et al. | |
| 4,727,020 A | 2/1988 | Recktenwald | |
| 5,674,698 A | 10/1997 | Zarling et al. | |
| 5,760,900 A | 6/1998 | Ito et al. | |
| 5,865,520 A | 2/1999 | Kavanagh et al. | |
| 5,930,048 A | 7/1999 | Kaneko | |
| 6,294,063 B1 | 9/2001 | Becker et al. | |
| 6,404,493 B1 | 6/2002 | Altendorf | |
| 6,510,007 B1 | 1/2003 | Blasenheim | |
| 6,558,945 B1 | 5/2003 | Kao | |
| 7,110,192 B2 | 9/2006 | Sauter et al. | |
| 7,523,637 B2 | 4/2009 | Roth et al. | |
| 7,738,099 B2 | 6/2010 | Morrell et al. | |
| 7,758,811 B2 | 7/2010 | Durack et al. | |
| 7,777,869 B2 | 8/2010 | Nerin et al. | |
| 7,952,806 B2 | 5/2011 | Callen et al. | |
| 8,077,310 B2 | 12/2011 | Olson et al. | |
| 8,101,426 B2 | 1/2012 | Durack et al. | |
| 8,619,370 B2 | 12/2013 | Hunter et al. | |
| 8,791,429 B2 | 7/2014 | Kim et al. | |
| 8,883,495 B2 | 11/2014 | Nakamura et al. | |
| 9,158,118 B2 | 10/2015 | Li et al. | |
| 9,423,348 B2 | 8/2016 | Norton | |
| 9,568,423 B2 | 2/2017 | Li et al. | |
| 9,575,063 B2 | 2/2017 | Li et al. | |
| 2005/0112541 A1* | 5/2005 | Durack ................ C12N 5/0612 435/2 |
| 2007/0096039 A1 | 5/2007 | Kapoor et al. | |
| 2008/0213915 A1 | 9/2008 | Durack et al. | |
| 2008/0283754 A1 | 11/2008 | Nerin et al. | |
| 2009/0116011 A1 | 5/2009 | Kenyon | |
| 2009/0141327 A1 | 6/2009 | Penn et al. | |
| 2010/0220315 A1* | 9/2010 | Morrell ............... G01N 15/1436 356/73 |
| 2010/0322064 A1 | 12/2010 | Kim et al. | |
| 2013/0095501 A1* | 4/2013 | Bueddefeld ............ C12Q 1/04 435/7.1 |
| 2013/0200277 A1 | 8/2013 | Li et al. | |
| 2015/0140577 A1 | 5/2015 | Li et al. | |
| 2016/0097707 A1 | 4/2016 | Li et al. | |
| 2017/0131206 A1 | 5/2017 | Li et al. | |
| 2017/0138856 A1 | 5/2017 | Li et al. | |
| 2018/0136107 A1 | 5/2018 | Li et al. | |

FOREIGN PATENT DOCUMENTS

| | | |
|---|---|---|
| CN | 102471752 A | 5/2012 |
| CN | 102998259 A | 3/2013 |
| WO | 2003/021241 A1 | 3/2003 |
| WO | 2010/099118 A1 | 9/2010 |
| WO | 2011/003073 A1 | 1/2011 |
| WO | 2011/140153 A1 | 11/2011 |
| WO | 2013/059835 | 4/2013 |
| WO | 2015/077349 | 5/2015 |
| WO | 2018/01403 A1 | 1/2018 |

OTHER PUBLICATIONS

EP12845835.3 European Search Report dated Jul. 1, 2015.
EP12841762.3 Extended European Search Report dated Mar. 27, 2015.
PCT/US2012/061399 International Search Report dated Jan. 9, 2013.
PCT/US2017/042284 International Search Report and Written Opinion dated Oct. 6, 2017.
EP14863825 Supplementary European Search Report dated Jul. 26, 2017.
Ramirez et al. "High-Throughput Flow Cytometry: Validation in Microvolume Bioassays." Cytometry Part A, 2003, 53A:55-65, Wiley-Liss Inc.
Scientiis International "Coming and Costar 96-well Cell Culture Plates" available on the company's webpage for product information, copyright 2005. http://scientiis.com/laboratorium/catalog/product_info.php?products_id=5574. retrieved from the internet on Dec. 9, 2016.

\* cited by examiner

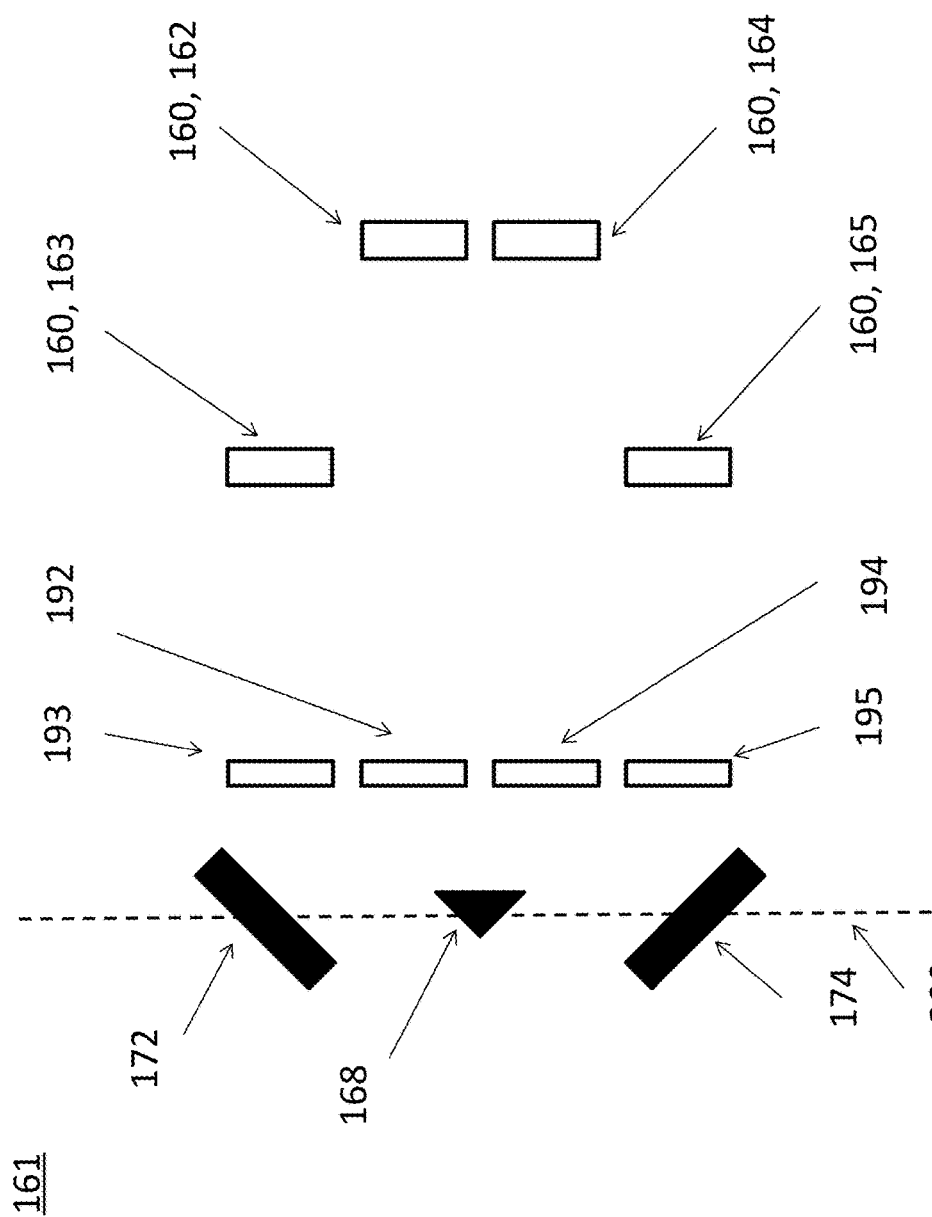

OPTICAL DETECTION SYSTEM FOR FLOW CYTOMETER, FLOW CYTOMETER SYSTEM AND METHODS OF USE

CROSS REFERENCE TO RELATED APPLICATIONS

This is a continuation in part of U.S. patent application Ser. No. 15/416,976, filed Jan. 26, 2017, which is a divisional of U.S. patent application Ser. No. 14/547,963, filed Nov. 19, 2014, now U.S. Pat. No. 9,575,063, which claims benefit of priority to U.S. provisional patent application Ser. No. 61/906,367, filed Nov. 19, 2013 and U.S. provisional patent application Ser. No. 61/994,980, filed May 18, 2014. Each patent application referenced in this paragraph is herein incorporated by reference in its entirety.

This application also claims benefit of priority to U.S. provisional patent application Ser. No. 62/363,032, filed Jul. 15, 2016; the entirety of which is herein incorporated by reference.

TECHNICAL FIELD

The invention relates to flow cytometry instrumentation and more specifically to an optical detection system that collects light including fluorescence from different vertical positions in a flow channel and separates collected fluorescence into a plurality of different detection channels according to wavelength range and by vertical position for selective detection.

BACKGROUND OF THE INVENTION

Flow cytometry is a laser-based, biophysical technology where fluorescent molecules coupled to cells are passed through a flow cell and excited by a set of lasers. The fluorescence is collected and separated into different channels with specific detection wavelengths, converted to electrical signals, and analyzed using a computer. By labeling cells with different fluorophores, various distinct cell populations can be resolved. For example, multi-color flow cytometry, such as three color flow cytometry uses fluorophores with different excitation and/or emission wavelengths to differentiate various cell subpopulations within biological samples.

Operationally, an excitation light is delivered to a flow cell by beam-shaping, steering, and guiding optical components. Passing fluorescently labeled cells or particles through the flow cell diffracts the light and excites the labels causing fluorescence. A complex design of multiple-lenses positioned at accurate locations relative to each other and relative to flow cell are employed to collect the fluorescent light and the diffraction light from the particles. The collected light is then split into different channels according to the particular excitation lasers and according to the light wavelength.

In one approach, different fiber optic cables are used to collect the fluorescent/scattered light as excited from different laser sources. Then the light from each fiber optical cable is split into different fluorescent channels. Alternatively, a specially designed objective is used to collect light from particles as they pass through different laser sources and the light is separated into different beams according to which laser source the light was generated and separated into different channels according to different dichroic mirrors.

All such collection optics are expensive to make, difficult to align, and difficult to adjust. Also, for many situations, the light collection efficiency is limited. Furthermore, the collected, split light is conventionally detected and measured with photo-multiplier tubes (PMTs). Whilst PMTs are widely used for flow cytometry applications and other optical measurement situations, they are expensive, bulky in size and complex to use. Therefore, there is a need for improved collection optics that are simple in design, have fewer optic components, have high light-collection efficiency, and have light detection/measurement sensitivity/efficiency.

SUMMARY OF THE INVENTION

The above deficiencies in flow cytometry design and technical approach are addressed by the present invention. In one aspect of the invention, an optical engine for use in a flow cytometer is provided, the optical engine including: a set of lasers, each tuned to a wavelength suited for excitation of fluorescent molecules, wherein light from each of the lasers is focused horizontally along an x-axis to a same horizontal position and vertically along a y-axis to a different vertical position along a same excitation plane, wherein the same horizontal position along the excitation plane intersects a flow path through a flow cell of a flow cytometer; a set of optics including collection optics for collecting fluorescence emitted from the flow cell and filtration optics that filter collected fluorescence from the flow cell into different wavelength ranges, wherein the set of optics further separate the fluorescence of a same wavelength range into different locations in a focal plane of the collection optics according to the different lasers by which the fluorescent light is excited; and a detector that selectively detects light from the different locations thereby distinguishing between fluorescence emitted within the same wavelength range as excited by different lasers within the set of lasers and converts light to an electrical signal. For the present application, light propagation direction for each laser is defined as Z-axis, which is perpendicular to the horizontal x-axis and to the vertical y-axis.

The optical engine permits the use of any number of lasers, but in some embodiments has at least two lasers, for example, two, three, four or five lasers, each of which is tuned to a different wavelength. In preferred embodiments, all the lasers are focused vertically along the vertical direction to different vertical positions of the flow cell. In one embodiment, the optical engine comprises a number of lasers, each emitting light at a specific wavelength suited for excitation of fluorescent molecules; a set of beam shaping optics for each laser, wherein each set comprises two lenses to adjustably focus light horizontally along an x-axis to a same horizontal position and vertically along a y-axis to a different vertical position along a same excitation plane, wherein the horizontal position on the excitation plane interests a flow path through a flow cell of the flow cytometer. In a preferred embodiment, a set of beam shaping optics comprises a set of cylindrical lenses (e.g., an x-axis cylindrical lens and a y-axis cylindrical lens) or a set of a Powell lenses (e.g. an x-axis Powell lens and an y-axis Powell lens). In another embodiment, the optical engine comprises a number of lasers, each emitting light at a specific wavelength suited for the excitation of fluorescent molecules; all the lasers' beams being independently adjustable horizontally along an x-axis and independently adjustable vertically along a y-axis, being combined together via suitably placed dichroic mirrors and going through a single achromatic beam shaping optic so that all the laser beams are focused to a same horizontal position and to different vertical positions along a same excitation plane, wherein the horizontal position on the excitation plane intersects a flow path through a flow cell of the flow cytometer. This embodiment is different from the example described where each laser has its own beam shaping optics.

In still other embodiments, the optical engine comprises a number of lasers, each emitting light at a specific wavelength suited for the excitation of fluorescent molecules. Optical design approaches different from above mentioned two embodiments are employed so that all the laser beams are focused to a same horizontal position and to different vertical positions along a same excitation plane, wherein the horizontal position on the excitation plane interests a flow path through a flow cell of the flow cytometer.

Focused laser beams at the excitation plane shall have beam sizes suitable for flow cytometry application. Generally, the vertical beam width at the excitation plane may vary from about two microns to about 20 microns. In one embodiment, the vertical beam width is between 2 and 5 microns. In another embodiment, the vertical beam width is between 5 and 20 microns. Preferably, the vertical beam width is between 5 and 15 microns. Generally, the horizontal beam width may vary from as about twenty microns to about 200 microns. In one embodiment, the horizontal beam width is between 20 and 50 microns. In another embodiment, the horizontal beam width is between 50 and 200 microns. Preferably, the horizontal beam width is between 50 and 100 microns.

Vertically focusing each of the multiple lasers (e.g., 2 lasers, 3 lasers, 4 lasers, 5 lasers or more) individually at different vertical positions along a flowing direction of the sample allows for distinguishing fluorescence excited by each of the multiple lasers by different photodetectors, as the spatial separation of the three different lasers along the vertical axis translates to time and positional differences of fluorescence emitted by particles when passing through each of the different lasers. Specially designed collection optics not only collect light from different vertical locations of the flow cell but also permit further separation of the light from different vertical locations as the light propagates through the filtration optics. The filtration optics, having optical components such as dichroic mirrors, band pass filters and/or other types of filters or lenses, can filter the fluorescence and light from the flow cell, into different wavelength ranges. Thus, light at each of these wavelength ranges is separated spatially along the vertical axis at a focal plane of the collection optics, thereby permitting fluorescence components within a same wavelength range to be distinguished during detection according to its originating laser. In some embodiments, the vertical separation between neighboring vertical positions of the focused beam along the excitation plane in the flow cells is between 60 and 200 µm. In other embodiments, the vertical separation between neighboring vertical positions of the focused beam in the flow cells is between 60 and 100 µm. In still another embodiment, the vertical separation between neighboring vertical positions of the focused beam in the flow cells is about 80 µm. The collection optics are able to amplify such separation distance to achieve a spatial separation of about a couple mm (e.g. a value between 1.5 and 2.5 mm), or about a few millimeters (such as about 3 mm, about 3.5 mm, about 4 mm or about 5 mm) between the neighboring vertical positions at the focal plane of the collection optics (each vertical position here corresponds to a light beam of particle fluoresce as excited by one corresponding laser). Spatial separation of adjacent beams at the focal plane of the collection optics permits fluorescent signal to be distinguished by wavelength range and originating laser using optical detectors.

In some embodiments, optical detectors are placed at the corresponding vertical positions along the focal plane of the collection optics, where each detector detects a light beam of particle fluoresce as excited by one corresponding laser. Such optical detectors can be arranged in a form of a detector array. In other embodiments, optical detectors are placed at some distances away from the focal plane of the collection optics, wherein each detector detects a light beam of particle fluoresce as excited by one corresponding laser. In still other embodiments, optical detectors are placed at some distances away from the focal plane of the collection optics and a lens is positioned along the optical path between the focal plane and the optical detector, wherein each detector detects a light beam of particle fluorescence as excited by one corresponding laser. Such a lens could serve the purpose of expanding the light beam from the focal plane and providing a relatively-uniform beam distribution.

In a preferred embodiment, the collection optics include a half ball lens followed by two sets of doublet lenses. Preferably, the half-ball lens is made of materials having a high refractive index. Preferably the combination of two sets of doublet lenses allow not only collection of light from different vertical positions in the flow cell but also further focus such light to a focal plane having larger separation distances of mm range, after light travels through filtration optics. The filtration optics can include long pass and/or short pass dichroic mirrors, bandpass filters, and other filters and/or lenses. In some embodiments, the filtration optics filter the collected fluorescence light (e.g. using a half ball lens and two sets of doublet lenses) into different wavelength ranges characterized as the following wavelengths 780/60 nm, 615/24 nm, 530/30 nm (or 530/43 nm), 445/45 nm, 586/20 nm (or 572/28 nm), 661/20 nm, 697/58 nm (or 695/40 nm), and 725/40 nm. Note that all the wavelengths have a unit of nm. The channel wavelengths cited here are for exemplary purposes only and are not intended for limiting the present invention.

Various methods can be used to distinguish light spots with mm-range separation at a focal plane of the collection optics. In one embodiment, such light spots are separated and focused to smaller sizes then coupled into a bundle of fiber optic cables. The light at the end of the fiber optic cables can be detected by a light detector such as a Photon Multiplier Tube (PMT), a silicon multiplier or multi-pixel photon counter (MPPC), or a photodiode. In another embodiment, such light spots at a focal plane of the collection optics are directly detected by a linear MPPC array, which comprises multiple MPPC chips, where each chip detects a corresponding light spot. In yet another embodiment, such light spots are further separated with additional optical components to even larger spatial distances between neighboring spots, to be detected or measured by a number of photo detectors such as a number of MPPC detectors, or a number of photodiodes, or a number of avalanche photodiodes, or a number of PMTs. In an exemplary embodiment, 4 lasers are employed as excitation sources with the vertical separation of 80 microns between neighboring vertically focused beams in the flow cell. The vertical separation distance between neighboring light spots at a focal plane of the collection optics is about a couple of mm (e.g. 1.5-2.5 mm) or a few millimeters (e.g., 3-5 mm). The two middle light spots are then further separated through a prism mirror, each to be detected by a MPPC detector. In particular, the two side light spots are directly detected by two MPPC detectors mounted at corresponding positions.

In other embodiments of the optical engine of the present invention, other approaches, different from the collection optics and filtration optics described above, could also be employed to collect, separate and split the fluorescent light and the scattered light from the particles flowing through the flow cell. In one embodiment, excitation laser beams of different wavelengths are delivered and focused to a flow cell by beam-shaping, steering, and guiding optical components. All the focused laser beams share a common horizontal position and would have different vertical positions in the flow cell where the flow channel is placed along a vertical direction. Passing fluorescently labeled cells or particles through the flow cell diffracts the light and excites the labels causing fluorescence. A complex design of multiple-lenses positioned at accurate locations relative to each other and relative to flow cell are employed to collect the fluorescent light and the diffraction light from the particles. The collected light is then split into different channels according to the particular excitation lasers and according to the light wavelength.

In one approach of light collection and separation, different fiber optics cables are used to collect the fluorescent/scattered light as excited from different laser sources. Then the light from each fiber optical cable is split into different fluorescent channels via use of different dichroic mirrors and bandpass filters. In another approach, a specially designed objective is used to collect light from particles as they pass through different laser sources and the light is separated into different beams according to which laser source the light was generated. Each separated light beam, originating from one laser source, is then separated into different channels according to the use of different dichroic mirrors and bandpass filters.

A detector for light detection (scattering light or fluorescent light) in the present invention is provided for each fluorescence channel, which is preferably in the form of a MPPC detector. Preferably, fluorescent light signal is converted to an analog electrical current signal by a MPPC, which is then converted to an analog electrical voltage signal through the use of a resistor. Still preferably, analog voltage signals are then converted to digital signals using analog to digital converter (ADC) and processed in digital form for increased accuracy and speed. In a preferred embodiment, each digital output data from the ADC is corrected or calibrated by dividing the data by a corresponding calibration factor, determined using the techniques described in the specification sections below. Preferably, the calibration factors allow the improvement of linear dynamic range by at least about half (0.5) decade. More preferably, the calibration factors allow the improvement of the linear dynamic range by at least about one (1) decade. Even more preferably, the calibration factors allow the improvement of the linear dynamic range by at least about one-and-half (1.5) decade. Even more preferably, the calibration factors allow the improvement of the linear dynamic range by at least about two (2) decades.

In another embodiment of the present invention, an optical engine for use in a bench top flow cytometer is provided, which comprises, a laser, tuned to a wavelength suited for excitation of fluorescent molecules, wherein light from the laser is focused horizontally along an x-axis to a horizontal position and vertically along a y-axis to a vertical position along an excitation plane, wherein the horizontal position along the excitation plane intersects a flow path through a flow cell of a flow cytometer; a set of optics comprising collection optics for collecting fluorescence emitted from the flow cell and filtration optics that filter the collected fluorescence from the flow cell into different wavelength ranges, thereby providing different fluorescent channels; and an MPPC detector at each fluorescent channel to detect fluorescence and convert light to an electrical signal. In a preferred embodiment, the optical engine further comprises a set of lasers, wherein each of the lasers is focused vertically along the y-axis to a different vertical position along the same excitation plane, further wherein the set of optics separate the emitted fluorescence from the flow cell into different fluorescence channels, wherein each channel is characterized by a different wavelength range and a different laser by which the fluorescence is excited.

In preferred embodiments of above optical engines, the MPPC is operated with a linear dynamic range above 3 decade. More preferably, the MPPC is operated with a linear dynamic range above 4 decade.

In some embodiments of above optical engines, the MPPC digital output value is corrected according calibration factors. Preferably, the calibration factors improve linear dynamic range of the MPPC by more than half decade. More preferably, the calibration factors improve linear dynamic range of the MPPC by more than one decade. Even more preferably, the calibration factors improve linear dynamic range of the MPPC by more than one and one-half decade. Still, even more preferably, the calibration factors improve linear dynamic range of the MPPC by more than two decades.

In a preferred embodiment, forward scatter (FSC) characterization of cells includes a FSC detector, a FSC focusing lens to collect FSC light, and an obscuration bar that blocks an incident laser beam from entering the FSC focusing lens and the FSC detector. The relationship between timing of fluorescence signal at a fluorescent light detector and timing of forward scatter signal at a FSC detector provides an approach for determining which laser induces excitation of a detected fluorescent signal in a detection channel.

Further improvement of forward scatter (FSC) detection has been achieved through the use of improved obscuration bars. In a preferred embodiment, a diamond shaped obscuration bar is provided. In another embodiment an obscuration bar that is of a rectangular shape and has its horizontal dimension being the same as or longer than its vertical dimension is provided for blocking the incident laser beam. In still another embodiment, the perimeter of the obscuration bar follows a contour of a light intensity distribution plot for blocking incident laser beam. In a still further embodiment, the obscuration bar follows a contour of a light intensity distribution plot within the 0.1% contour line. A 0.1% contour line or boundary corresponds to a line where the light intensity at each point on the contour is at 0.1% of maximum light intensity of the incident light. An obscuration bar following the contour of a light intensity distribution plot within the 0.1% contour was determined to block 99% of the unscattered beam from the FSC detector. Accordingly, the invention also provides an obscuration bar generally diamond shaped that follows a contour of a light intensity distribution plot within the 0.1%, 0.2%. 0.5%, 1.0% or 2.0% contour line and methods of its shaping.

Components of the optical engine are preferably housed as a single unit, and some of these optical components can be removed and interchanged for modification with other components. To this end, a housing configured to house optical engine components is also provided. The housing includes the optical engine components such as the set of lasers, the optics for focusing laser beams to the excitation plane, collection optics, filtration optics, photo-detectors or light-detectors, further filters (and/or lenses), as well as an electrical interface for electrical connection from the photodetectors or light-detectors to electrical circuitry, which would be connected to an external microprocessor or a remote computer. In some embodiments, each laser has a corresponding set of beam-shaping optics wherein light from each laser is focused horizontally along an x-axis to a same horizontal position and vertically along a y-axis to a different vertical position along a same excitation plane, wherein the same horizontal position along the excitation plane intersects a flow path through a flow cell of a flow cytometer. In other embodiments, all the laser beams being independently adjustable horizontally along an x-axis and independently adjustable vertically along a y-axis, are combined together via suitably placed dichroic mirrors and go through a common achromatic beam shaping optics so that all the laser beams are focused to a same horizontal position and to different vertical positions along a same excitation plane, wherein the horizontal position on the excitation plane interests a flow path through a flow cell of the flow cytometer. Preferably, the components within a same housing are configured for interchangeability of different lasers, focusing lenses, long pass and short pass dichroic mirrors, filters, pinhole passages and detectors. This is accomplished by standardizing engagement features such as positioning of alignment holes, snaps, screws or other fasteners across different components for interchangeability and by providing a set of beam shaping optics for each laser individually. Preferably, the photo-detectors or the light detectors are MPPC detectors. In some embodiments, a flow channel is mounted in the housing and configured for coupling to a flow cytometer apparatus for hydrodynamic focusing of samples including particles (e.g. beads or cells) by tubing connectors.

In a related embodiment, the invention also includes a flow cytometer, which includes any of the optical engines as disclosed herein; a flow channel; and a pump in fluid communication with an aspiration needle for aspirating and delivering a suspension of cells through the flow channel. In a preferred embodiment, the flow cytometer is further characterized in that there are two (2), or three (3), or four (4) or five (5) lasers, each tuned to a different wavelength and focused to a different vertical position of the flow cell; a set of optics including collection and filtration optics for collecting and filtering light from the flow cell; and where the set of optics spatially distinguish and separate the filtered fluorescence in the same wavelength range, that is excited by each of the two, three, four or five different lasers, to different vertical locations along a focal plane of the collection optics.

In a preferred embodiment, the flow cytometer is further characterized in that there are four lasers, each tuned to a different wavelength and focused to a different vertical position of the flow cell (i.e., total four vertical positions in the flow cell); collection optics for collecting light from the flow cell and filtration optics for filtering the light; and wherein the collection optics and filtration optics spatially distinguish and/or separate the filtered fluorescence based on the vertical position of the focused excitation beam to different vertical locations in a focal plane of the collection optics (i.e. also four distinct vertical positions in the focal plane). Light spots at such a plane would be, optionally further separated, and detected by a number of MPPC detectors, or a MPPC array. To this end, a flow cytometry apparatus is provided which includes up to 25 fluorescent color channels for particles or cells passing through the flow cell in addition to side scatter and forward scatter measurement.

In a related embodiment a flow cytometry system has been developed, which includes a flow cytometer as provided herein; and a software for loading and execution in a computer to acquire and analyze flow cytometry data. As such, flow cytometry software for loading in a computer has also been developed. In some embodiments, the software provides programming to perform the following functions: collecting data from fluorescence channels for each detector, wherein the fluorescence signals collected by different detectors are converted to different data series, corresponding to the fluorescence excited by lasers at the different vertical positions; generating a graphical user interface (GUI) that displays various plots for the acquired data, wherein the GUI further comprises compensation scroll bars adjacent to the comparison plots to adjust compensation of spectral overlap between one or more channel; acquiring the data from the cytometer and saving the data as a data file into the computer hard drive. The software also includes a gating function that permits the user to select a subpopulation from a data plot and generate additional plots for the selected subpopulation. This process can be performed repetitively for all fluorescence channel data as well as side scatter and forward scatter data.

In still another related embodiment a flow cytometry method is provided, which includes providing flow cytometry system as provided herein; labeling a suspension of cells with a plurality of fluorescent labels; pumping the sample of cells through the flow cell; collecting flow cytometry data; and analyzing the flow cytometry data to determine the presence, absence or abundance of one or more of the plurality of fluorescent labels on or in cells of the sample.

BRIEF DESCRIPTION OF THE DRAWINGS

FIG. 6B is a schematic showing a configuration for detecting four fluorescent light beams broadened by a lens 192 (193, 194 or 195) for detection at detector 162 (163, 164 or 165).

DETAILED DESCRIPTION OF PREFERRED EMBODIMENTS

Figure 1:
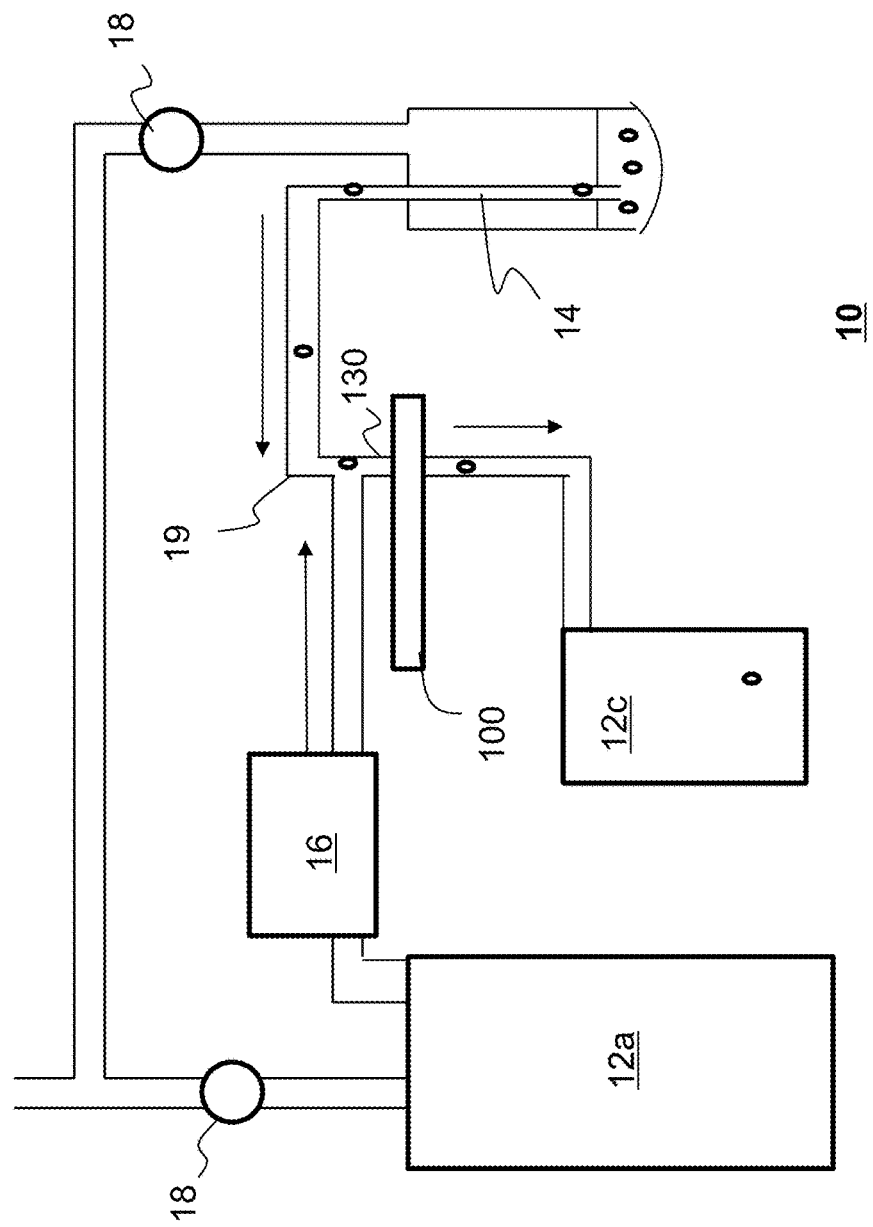
FIG. 1 is a schematic providing an overview of transfer of a cell suspension through the optical engine 100.

The invention provides a flow cytometer and its optical engine that is individually configurable and expandable by interchangeable lasers, optics configurations and detectors that provide measurement of up to many parameters, including a large number of color fluorescence channels, of many individual particles in a single sample. The interchangeability of the components within the optical engine permits the user to tailor the excitation and detection channels according to unique experimental conditions and according to individual needs. This allows the user to add or substitute components within a same flow cytometer while maintaining high detection sensitivity and resolution. The improved detection sensitivity and resolution is further made possible by incorporating a multi-pixel photon counter (MPPC) that has high photon-electron conversion efficiency, yet overcomes the shortcoming of MPPC devices, namely, larger dark-count and larger background noises and narrow dynamic ranges.

The flow cytometer, includes an optical engine, which is described in various nonlimiting embodiments herein; a flow channel; and a pump in fluid communication with an aspiration needle for aspirating and delivering a suspension of cells through the flow channel. The pump fluidics are shown to reproducibly deliver cells through the flow channel at high speed to reproducibly conduct sample acquisition rates of over many thousands events/second. Further, with the add-on autosampler, optional shaker, and sample collection methods as provided in U.S. Pat. No. 9,575,063 and US 2016/0097707, each of which is herein incorporated by reference in its entirety, such rates can be achieved together with automated sample feeding to the aspiration needle. In addition, the flow cytometer is programmed with features such as autocleaning of the aspiration needle to reduce likelihood of sample carryover and cross-contamination.

In a preferred embodiment, the optical engine within the flow cytometer is further characterized as having a set of lasers, such as from single to multiple lasers (e.g., 2 or 3 or 4 or 5, or even more), each tuned to a different wavelength suited for excitation of fluorescent molecules. In some embodiments, improved focusing of each of the plurality of laser beams to distinct locations along the flow cell is accomplished by providing a set of beam shaping optics for each laser, wherein each set preferably includes two lenses to adjustably focus light horizontally along an x-axis to a same horizontal position and vertically along a y-axis to a different vertical position along a same excitation plane, the plane being characterized as being within a flow path through a flow cell of the flow cytometer. For the beam shaping optics described here, the laser light propagation direction is defined as Z-axis, which is normal to the horizontal x-axis and vertical y-axis. Beam shaping optics preferably include cylindrical lenses so that the focused beam is at the center line in the flow cell and of elliptical shape. By assigning beam shaping optics to each laser, each laser can be precisely focused to a different vertical position of the flow cell thereby eliminating the tradeoffs associated with configurations that require sharing beam shaping, steering and guiding optics between lasers as commonly provided in commercially available systems.

In related embodiments, multiple lasers share certain beam-shaping optics components and at the same time, each individual laser can be focused and steered or guided to different vertical positions along a same plane. Those skilled in optics design may develop such optical illumination systems with the guidance herein.

In preferred embodiments, a set of optics is provided, which includes collection optics that collect particle-scattered light and fluorescence from the flow cell and filtration optics that filter the collected fluorescence (collected by the collection optics) emitted from the flow cell into different wavelength ranges, wherein the set of optics further separate the fluorescence of a same wavelength range into different locations according to the lasers by which the fluorescent light is excited; and a detector that detects light from each of different locations, each excited by one individual laser, thereby distinguishing between fluorescence emitted within the same wavelength range from different lasers within the set of lasers and converts light to an electrical signal.

It is important to note that the collection optics and filtration optics not only collect particle-scattered light and fluorescence from the flow cell but also filter the collected fluorescence from the flow cell into different wavelength ranges. Furthermore, the collection optics and filtration optics take advantage of separated laser focal points along the flow cell (also referred to as within the excitation plane) for different lasers, allowing the separation of fluorescent signals of same wavelength ranges as excited by the different lasers into different locations where a detector is employed to detect and measure fluorescent light excited by each different laser.

Fluorescence signals and scatter signals can be detected with various optical detectors. Focusing the lasers at distinct positions along the flow cell for excitation permits comparisons between the timing of fluorescence signals at each detector at different wavelengths and forward scatter signals, which help construct the light signals (the scatter light, forward scatter and side scatter, and the fluorescent signals at different wavelengths and excited by different lasers) into data sets corresponding to individual cells or particles going through the excitation plane in the flow cell. Note that the data sets are digital signals that are converted from analog electronic signals obtained through light detectors that convert light into electronic signals.

For example, for a 3 laser system having red, blue and violet lasers, the laser beams are focused to 3 different vertical locations along the flow cell, ordered as red, then blue, then then violet counting from a lower position to a higher position. Consider a particle is labelled by a number of different fluorescent dyes, where two fluorescent dyes are excited by violet laser, emitting light at ~450 nm and ~780 nm, two fluorescent dyes are excited by blue laser, emitting light at ~530 nm and ~780 nm, and one fluorescent dye is excited by red laser, emitting light at ~780 nm range. As the particle moves through these 3 laser beams, the fluorescent light at ~780 nm induced by red laser excitation would be ahead the fluorescence at ~780 nm and the fluorescence at ~530 nm induced by a blue laser, which is then followed by the fluorescent light at ~780 nm and at ~450 nm induced by a violet laser. Assuming that a forward scatter is detected for particles passing through the blue laser beam, the timing of forward scatter for a particle would coincide with the ~780 nm and ~530 nm fluorescence induced by blue laser. Similarly, assuming that a side scatter is detected for particles passing through the blue laser beam, the timing of side scatter for a particle would coincide with the ~780 nm and ~530 nm fluorescence induced by blue laser. Note that the collection optics would collect the side scatter and all fluorescence at different wavelength ranges (i.e. ~450 nm, ~530 nm, and ~780 nm range) excited by the three lasers. The filtration optics would split the collected fluorescence into light with wavelength around 450 nm, light with wavelength around 530 nm and light with wavelength around 780 nm. Light detectors are then placed to detect fluorescence at 450 nm and 530 nm respectively. In addition, with collection optics and filtration optics, the filtered light with wavelengths around 780 nm would be separated into three different locations according to the laser by which the fluorescence is excited. Then three different detectors can be employed so that each is to detect the fluorescence (at ~780 nm range) each excited by one laser. In one exemplary embodiment, these different locations are separated by a couple mm to a few mm apart within a focal plane of the collection optics (as the fluorescence is being collected from the flow cell and, being filtered and focused down onto a focal plane of the collection optics). In another embodiment, the fluorescence separated by a few mm could be further separated into even larger distances, for example 5-10, or 10-20 mm apart.

In the above example, optical detectors can detect forward scatter, side scatter, as well as fluorescence at 450 nm range (excited by violet laser), fluorescence at 530 nm range (excited by blue laser), and three different fluorescence at 780 nm range excited by red laser, blue laser and violet laser, respectively. Signal processing approaches and algorithms assign and combine the signals obtained from each detector into data sets that belong to a single cell or particle.

The flow cytometer is preferably provided as part of a flow cytometry system, which includes computer software for acquiring and analyzing flow cytometry data. The flow cytometry software operably communicates the flow cytometer to a computer and provides a variety of easy to use features. Among these include slideable compensation scroll bars positioned adjacent to corresponding fluorescent channels on displayed data plots, an easy to use experiment manager, and improved laboratory reports showing gated populations and corresponding counts.

A preferred flow cytometry system includes configurable detection fluorescence channels; 1 to 5 or 6 lasers; optimized detector conditions, automated fluid-maintenance functions; syringe pump sampling fluidic system; novel optical design, with enhanced signal detection as a powerful analytical tool for cell-by-cell discrimination. This system permits reliable quantitative measurements and rapid acquisition of statistically significant data for high density, multiplexed assays.

Many of the improvements described herein have been achieved, in part, are due to the adaptation of a multi-pixel photon counter (MPPC) chip for detecting fluorescent light. Compared to photomultipler tubes (PMTs) widely used in flow cytometry, MPPC technology presents some distinguishing features, such as a smaller foot print in size and larger quantum efficiency, allowing the measurement of low light signals. MPPC, as also known, silicon photomultiplier (SiPM), is a solid state device with an array of avalanche photodiodes (APD) operated in the Geiger mode. When operating in the Geiger mode, sufficiently large electrical charge output is produced at each individual APD even when a single photon excites it. Each pixel is a combination of an avalanche photodiode (APD) operating in Geiger mode and a resistor (referred to as a "quenching resistor"), where the APD is placed in series with the resistor. In operation of using MPPC for light detection, the light beam (fluorescence or scattered light) is directed to the MPPC surface. MPPC output as a result of receiving the incident light beam is in a form of electrical current, which is then converted to an analog voltage signal. The analog voltage signals, preferably, are converted to digital signals using an analog to digital converter (ADC) and processed in digital form for increased accuracy and speed. Whilst the digital output data is not directly from the MPPC detector/device, for simplicity in the present document and invention, we sometimes refer the digital data from the ADC or from digital circuits after ADC as the MPPC output data itself. It is worthwhile to point out the incident light beam to MPPC surfaces may be a constant light beam, or in many applications including flow cytometry applications, the incident light beam may be of a pulse form, and as such, the MPPC output would also take the form of a pulse, that is the output is time-dependent. Here the MPPC output includes the time-dependent electric current from MPPC, or the time-dependent analog voltage after current-to-voltage conversion, or the time-dependent digital data after ADC.

Whilst MPPCs could theoretically be used in flow cytometry to detect and measure fluorescent light, it has not been used in practical cytometers, due to a number of technical challenges:

1) MPPC has a large dark-count background. Such a large dark count background presents a limiting factor for detecting dim fluorescent signals. Furthermore, such dark count could be temperature dependent.

2) MPPC gain, dependent on the operational voltage applied to a MPPC, is very much temperature dependent. Temperature fluctuation could result in a change in light signal amplification gain. This is different from PMT where temperature does not have a large influence on the PMT gain.

3) MPPC's linear dynamic range in terms detecting and measuring light of different intensities is limited, as mainly dependent of number of pixel in the MPPC. A wide dynamic range covering many decades of light intensity is required for detectors usable for flow cytometry applications.

Challenges associated with MPPC's temperature dependent, large dark-count, have been overcome by effectively reducing and controlling the dark-count noise by designing and developing an apparatus to lower and/or stabilize the operational temperature of MPPCs. By securing control of MPPC's operating temperature, the MPPC's gain during operation has now been stabilized. Further an un-expected 'by-product' effect of lowering the operational temperature of the MPPC is that is we have achieved a large dynamic range since the low end light detection is mainly determined by the dark-count.

Whilst MPPC's linear dynamic range is limited when using conventional flow cytometry optics' configurations with conventional light detectors (e.g. namely PMTs), we have developed an approach to manipulate the beam size at the MPPC sensor surface to maximize usage of MPPC light-detection area for all filter channels and to provide sufficient dynamic range of light detection.

As described above, various approaches commonly-used to separate and split light could also be employed to separate, split and collect the fluorescent light and the scattered light from the particles flowing through the flow cell. Among these include beam-shaping, steering, and guiding optical components.

Configuring a set of optics having multiple-lenses at precise locations relative to each other and relative to flow cell can be employed to collect the fluorescent light and the diffraction light from the particles. The collected light is then split into different channels according to the particular excitation lasers and according to the light wavelength. The light beam at each fluorescent channel due to one excitation laser and with a particular wavelength range can be detected with a MPPC with an appropriate beam size through the use of different optical lenses for focusing or expanding the light beams.

In one approach of light collection and separation, different fiber optics cables are used to collect the fluorescent/scattered light as excited from different laser sources. Then the light from each fiber optical cable is split into different fluorescent channels via use of different dichroic mirrors and bandpass filters. The light beam at each fluorescent channel with a particular wavelength range can be detected with a MPPC with an appropriate beam size through the use of different optical lenses for focusing or expanding the light beams.

In another approach, a specially designed objective is used to collect light from particles as they pass through different laser sources and the light is separated into different beams according to which laser source the light was generated. Each separated light beam, originating from one laser source, is then separated into different fluorescent channels according to the use of different dichroic mirrors and band-pass filters. Similar to above, the light at each fluorescent channel with a particular wavelength range can be detected with a MPPC with an appropriate beam size through the use of different optical lenses for focusing or expanding the light at such channel.

In one embodiment of the present invention, the optical engine comprises a set of optics, which includes collection optics and filtration optics that separate fluorescence of a same wavelength range into different locations in a focal plane of the collection optics according to the lasers by which the fluorescent light is excited. Preferably, the optical engine further comprises a lens for expanding the beam size of fluorescence light of the same wavelength range from each of different locations of the focal plane of the collection optics, each originating from the fluorescence excited by an individual laser, to about a size between 1 mm to 3 mm, at the MPPC surface. Optionally, the beam size at MPPC surface is between 1.5 and 2 mm. Whilst it is desirable to utilize the largest beam size possible on a MPPC surface, compromise may have to be developed for positioning tolerance/accuracy. In addition, for increasing linearity dynamic range of MPPC surface, a properly developed/designed lens would allow a relatively-uniform beam be achieved on the MPPC surface.

By developing optic lenses matched with the fluorescence light previously separated by the different locations of the focal plane of the collection optics, relatively-uniform beam with suitable sizes can be achieved at chosen MPPC surfaces. Surprisingly, such a beam uniformity (less than 10% variation in the light intensity across the beam size) and such a beam size (about 70% in single dimension, relative to a MPPC width/length, e.g. 3 mm, or 6 mm) could be obtained for the fluorescence light of all the wavelength ranges. i.e for all fluorescent channels for the optical collection system and the properly designed optic lens here. Together with such beam characteristics at MPPC surfaces, appropriately applied operational voltages on MPPC (affecting the gain and dark-count of MPPC) and suitably controlled temperature range (affecting the dark count), a reasonable linear dynamic range can be observed. For a number of commercial available MPPCs, we have been able to obtain a linear range from about 3 decades, about 4 decades, to about 5 decades, under a single operational voltage, for different MPPCs. Such a surprisingly positive result of an MPPC providing about 3 decades, about 4 decades, or above linear dynamic range, as described here, can be achieved only through the development of associated optics allowing suitable beam size, uniform beam distribution, controlled dark counts etc. To be clear, in the present invention, each decade corresponds to a factor of ten, thus 3, 4, and 5 decades correspond to a factor of 1,000, 10,000 and 100,000, respectively. In other words, a linear range of 3, 4 and 5 decade means that the MPPC output goes linearly with the intensity of the incident light for the linear dynamic response range where the ratio of its maximum to its minimum light intensity value is 1,000, 10,000 and 100,000, respectively.

To further improve the linear dynamic range of an MPPC, additional technological approaches are required. As discussed above, MPPC's linear dynamic range in terms detecting and measuring light of different intensities (i.e. the outputting-electronic current as a result of incident light) is mainly dependent of number of pixels in the MPPC. Specifically, a given pixel within an MPPC can be activated by an incident photon (with a probability less than 1 for such activation, this probability is the Quantum efficiency for the MPPC detector), resulting a nano-second range response pulse in the output electronic current. At basic physics level, such an activation in a MPPC pixel is the status where the avalanche photodiode (APD in this pixel) operates in Geiger mode under an operational bias voltage, in series with a quenching resistor. During such nano-second range response time (dependent on pixel capacitance and quench resistance), an additional photon arriving at the same pixel will not be able to activate the pixel. Thus, in theory and in practice, at any given instant or within a short time window of nano-seconds range, the maximum number of pixels for an MPPC that can be activated (that are being activated) by the incident photons for electronic current output is the number of pixel within the MPPC, and any more photons (more than the number of pixels for the MPPC) arriving at MPPC surfaces will not be able to activate more pixels and will not contribute to additional electronic current output. This is the main cause of the limitation for MPPC's linear dynamic range of electrical current output in relationship to the input light (at MPPC surface). Some additional factors, other than pixel numbers of a MPPC detector as well as MPPC's quantum efficiency for photon detection, that could influence the dynamic ranges, include the dark count (or dark current), the MPPC gain (the ratio of electrical charge of the response pulse generated from one activated pixel due to one incident photon, divided by the charger per electron), the cross-talk factor (the cross talk refers to an effect where an activated pixel that detects a photon for output charge pulses may affect other pixel, causing them to produce output electric charge pulse). At the experimental level, an operational bias voltage on MPPC would affect all above factors, including quantum efficiency, the dark current, the gain as well as crosstalk factor.

To further improve the dynamic range of a MPPC so that the output current is linearly proportional to the light intensity over a wide intensity range, a numerical calibration technique has been developed in the present invention. The technique is based on the fact that at relatively high level of incident light intensity to MPPC surfaces, the output current from MPPC may saturate and would be lower than the ideal situation where all the incident photons could generate an output electric charge pulse. If the ratio of the actual output current from an MPPC to the theoretically-ideal output current can be determined at each and all light intensity for these high light level situations, these ratios could be used to calibrate the MPPC detector output by dividing the measured MPPC output data by such ratios. We term these ratios 'calibration factors'.

The approach to derive the calibration factors has been developed, as following. For a given MPPC type, a number of standard light beams are designed and produced through choice and designs of optical source (e.g., laser, laser diode, light emitting diode), beam shaping optics (e.g. spherical, aspherical, cylindrical lenses), light intensity attenuation mechanism (e.g. neutral density filters that have a constant attenuation across the range of visible wavelengths, beam cutting pinholes, as well as control voltages on the light source that may modulate the output intensity levels of light source), the light wavelength range (e.g. Band pass filters, light sources of given wavelength ranges), the light pulse shape or waveform. These standard light beams could be reliably and consistently produced having the desired beam size and beam uniformity by using the appropriately designed beam shaping optics. The beam quality parameters including beam size and beam distribution uniformity should match, or be the same as, those of the fluorescence or scattering light to be detected in the optical engine or the flow cytometer of the present invention. The standard light beams can have different wavelength ranges, for example, 515-545 nm, 650-670 nm, etc, which should match the wavelength ranges used for optical detection (scattering or fluorescence) in the optical engine and the flow cytometer. The light intensity of the standard beam can be adjusted, having a range of intensity from sub-milli-watts, to microwatts, to nano-watts or pico-watts, or even femto-watts ranges, which should match the light intensity range that will be detected by an MPPC in the optical engine or the flow cytometer of the present invention. The light pulse shape or waveform is designed and controlled so that they would match the light pulse waveform that is detected at an MPPC in the optical engine or the flow cytometer of the present invention.

The light intensities of such a number of standard light beams are measured and determined using certain optical detectors having a good wide dynamic range and an excellent linearity response. Such optical detectors may be chosen from a PMT (photon multiplier tube) and an APD (avalanche photon diode). These optical detectors may not have sufficient detection sensitivity or linearity for accurately measuring low light intensity beams. To ensure an accurate determination of light intensities of all standard light beams covering a wide intensity range, the low intensity-level beams could be produced by one or multiple light attenuation filters (e.g. neutral density filter having Optical Density (OD) 0.5 or OD 1, optical density is the negative of the common logarithm of the transmission coefficient) and such beam intensities could then be calculated based on the OD numbers of the filters as well as the measured light beam intensity before going through OD filters. Thus, we have been able to produce a range of standard beams with quantified light intensity levels. In other words, for a range of target light intensity levels, we can operate light sources, change optic paths and adjust various possible conditions (e.g. voltage applied to light source, or adding or removing certain light attenuation filters) to produce light beams (of desired size, uniformity, wavelength) to meet these target intensities.

With the capability for reliably producing such a number of standard light beams, MPPC of interest is used to measure these standard beams at a given operational bias voltage for the MPPC. MPPC, together with its associated circuits, including current-to-voltage conversion, as well as analog-to-digital convertor (ADC) and any possible analog or digital filters, will provide a series of output digital data, each, corresponding to a light intensity level of a standard light beam. Thus, a plot of MPPC digital output versus the light intensity levels could be obtained for such a number of standard light beams. At the intensity range of low light levels but still a few times above dark-count of the MPPC detector, an excellent linearity can be obtained (observed, as expected) between the MPPC output data and light-intensity level. Based on the slope (the measured MPPC data is in Y-axis, the light intensity is in the x-axis, a slope can be derived based on linear regression for a number of data points) in this good linearity range, it is possible to obtain theoretical MPPC output data for all the light intensity beams as the product of the slope (in the above linearity range) and the light intensity values for each standard beam.

Thus, a calibration factor for each measured MPPC value can be obtained by dividing the measured MPPC data by theoretical MPPC data for each of standard light beams. Mathematical modelling or simulation can be then undertaken to derive a calibration factor equation so that for any measured MPPC data, a calibration factor is determined and used to calculate the 'theoretical, calibrated' MPPC output data. As such, the non-linearity of MPPC output versus input-light intensity can be corrected or calibrated so that an extended wide-dynamic range is possible.

In above paragraphs, we have described the process to derive calibration factors for calibrating the MPPC output data based on use of a number of standard light beams with a range of intensities. The above approach is not intending for limiting the technique or methods for deriving or utilizing such calibration factors for extending the dynamic range of an MPPC detector. Indeed, there are other possible methods or approaches to derive the calibration factors. Regardless the approaches, the calibration factors, being the ratio between the measured, linearity-limiting MPPC values and the ideal, theoretical MPPC values that are expected from an ideal, linearly-responding MPPC.

It is worthwhile to point out that the calibration factors or calibration factor curves would be dependent on MPPC types—different MPPC types would have different calibration factor curves. Calibration factor curves are also dependent on operational bias voltages applied to an MPPC and operational temperature. Furthermore, the calibration curves depend on the size and uniformity distribution of light beams on the MPPC surfaces, as well as on the wavelength ranges of the light beam.

In preferred embodiments of the optical engine employing MPPC detectors, each MPPC output data is scaled up by dividing the data with a corresponding calibration factor, for the purposes of improving linear dynamic range of the MPPC detectors. The calibration factors are determined using the techniques described above. Preferably, the calibration factors allow the improvement of linear dynamic range by at least about half (0.5) decade. More preferably, the calibration factors allow the improvement of the linear dynamic range by at least about one (1) decade. Even more preferably, the calibration factors allow the improvement of the linear dynamic range by at least about one-and-half (1.5) decade. Even more preferably, the calibration factors allow the improvement of the linear dynamic range by at least about two (2) decades.

In view of the above, the invention is described in still more detail with reference to the following non-limiting embodiments. Turning first to FIG. 1, a pump 16 drives sheath fluid to a flow cell 130, into which a sample is also delivered by other known mechanisms such as a pump (e.g. a syringe pump). The sample, conventionally embodied as a suspension of particles (e.g. cells), is hydrodynamically focused by the sheath fluid into the center of the flow cell. The ordered passage of cells through different excitation lasers generates fluorescent light, which is detected by detectors following light collection and light splitting optics, collectively referred to as a set of optics. There are various methods and approaches for driving and delivering sheath fluid and sample fluids containing suspensions of cells into a flow cell for hydrodynamic focusing of sample fluid. These are well known in the flow cytometry arts and are typically accomplished using a combination of pumps 16, valves 18 and flow passages 19.

The flow cytometer 10 can be operated manually such as by individually providing a suspension of cells tube-by-tube to the flow cytometer 10, through aspiration via a sample aspiration needle 14 (FIG. 1) as known in the flow cytometry arts, or may be adapted for high throughput through the incorporation of an optional modular autosampler. Such a modular autosampler is preferably compatible with different loading tubes. Among these include racks of conventional 12×75 mm flow tubes, 1.5/2.0 mL tubes, such as those commonly manufactured by Eppendorf International, multi-well plates, such as 24 well, 96 well, (even 348 well), flat bottom, V-bottom, round bottom or any other suitable tube or dish for maintaining a suspension of cells. In preferred embodiments, the autosampler is equipped with a shaker for sample agitation or other mechanisms for sample mixing. In preferred embodiments the autosampler includes self-alignment protocols for ease of setup and maintenance, allowing convenient installation by users.

In preferred embodiments the flow cytometer 10 includes a microprocessor (i.e. one or multiple microprocessors) to control a variety of functions, such as fluid or sample delivery, cell suspension or shaking, and self-alignment of sample vessels. The microprocessor is typically provided on a circuit board, coupled to memory and electrically connected to electric mechanisms such as electric pumps and actuators to accomplish the intended function. Further, the microprocessor may modulate voltages to the detectors, lasers, aspirating pump or other electrical components. The microprocessor may include an analog to digital converter for converting analog signals from the photodetectors to digital signals. The microprocessor may process and analyze the digital signals for different scatter channels and different fluorescent channels to produce a data set for individual cells or particles. The microprocessor is communicatively connected to a computer, which provides various control commands to the microprocessor and receives the data from the microprocessor, controlled by the developed software.

Preferred embodiments include executable control programs stored in the microprocessor for automated sample aspiration needle 14 cleaning (when a clean command is received from the computer connected to the cytometer) after every sample aspiration to reduce risk of cross contamination of cell suspensions. This is still more preferred when using an autosampler. This is accomplished by controlling various pumps and valves for cleaning external and internal surfaces of the aspiration needle(s) 14 with sheath fluid or rinse fluid. Preferably such a feature should result in less than 1%, or 0.5%, even more preferably 0.1% or 0.05% carry over in embodiments using such an autosampler.

Preferred embodiments also include an automated de-bubble and unclogging feature, which prevents erroneous results from bubbles or clogs in the fluidic flow of cell suspensions and further ensures accurate direct absolute counts without needs of expensive reference counting beads. In preferred embodiments, the flow cytometer 10 also includes an automated cleaning function at start up and shut down of the flow cytometer 10. This programming improves the ease of use and removes the need of the user to perform these steps, which can be tedious and time consuming. In still further embodiments an automatic fluid level detection alarm, such as in the form of a suitable fluid-level sensor is incorporated to inform the user when system fluid levels are low.

Figure 2:
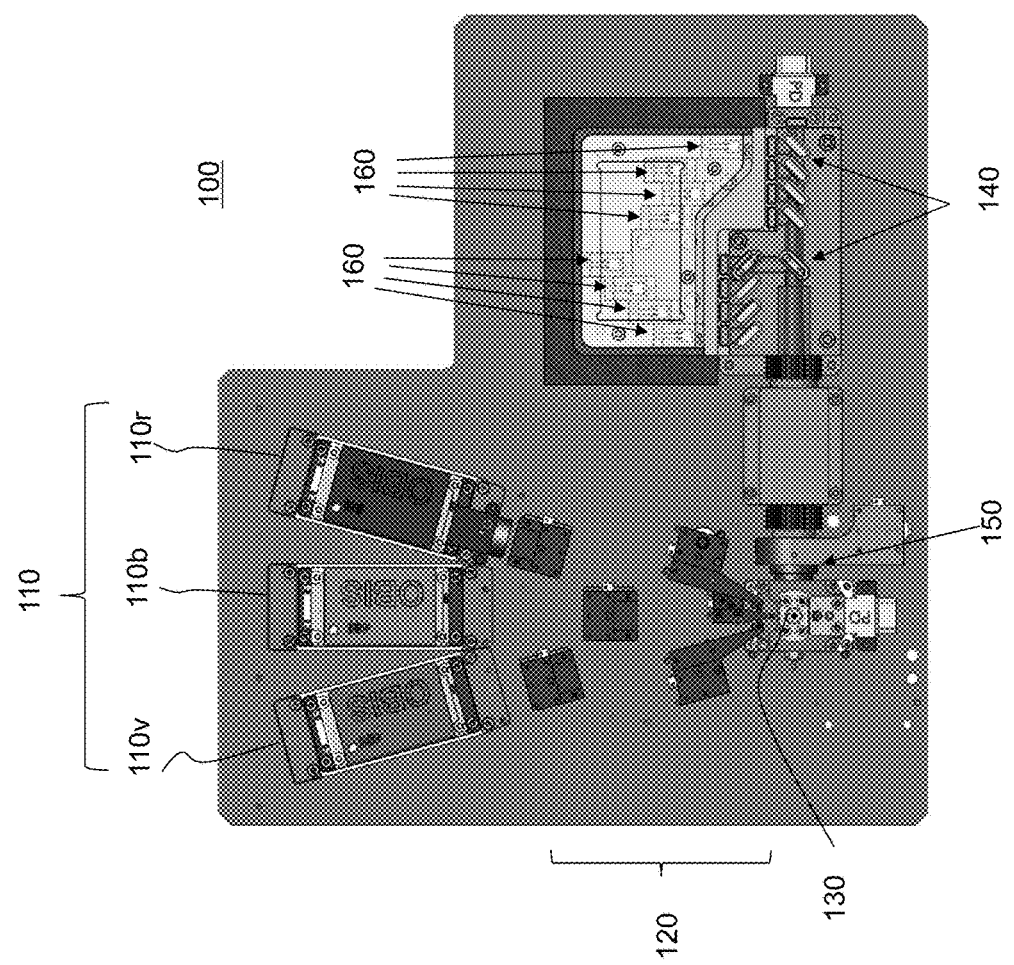
FIG. 2 is a top view of a representation showing an exemplary optical engine 100.

Turning to FIG. 2, a schematic providing an overview of an exemplary optical engine 100 is shown. The optical engine 100 includes from one to three lasers 110, and a set of beam shaping optics 120 for each laser 110 to independently shape and guide each excitation light source to the flow cell 130. Fluorescence is collected by collection optics 150, and separated into different wavelength ranges by filtration optics 140. Detection of fluorescence is accomplished using a MPPC detector 160 for each channel. Many electronic components including one or more microprocessors for operation of the flow cytometer 100 including automated system functions in response to commands from the developed control software, electronic circuits for operating light detectors and for converting analog to digital signals and for processing the digital signals etc. are not shown in FIG. 2 for simplicity. The syringe pump fluidics in fluidic connection with flow cell 130 during operation is also not shown here.

Although the optical engine 100 may use a single laser 110, the optical engine 100 permits the flow cytometer 10 to perform multicolor flow cytometry analysis such as by measuring a large number of parameters and a number of fluorescence signals from each fluorescently labeled cell. This can be achieved with, for example, three lasers 110v, 110b, 110r in FIG. 2. Conveniently, lasers 110 can be added, removed, or interchanged at least in part due to the individually assigned collection optics 150. An exemplary configuration for multi-color flow cytometry is shown in FIG. 2, including a first laser 110v emitting a wavelength of 405 nm (also referred to as violet laser), a second laser 110b emitting a wavelength of 488 nm (also referred to as blue laser), and third laser 110r emitting a wavelength of 640 nm (also referred to as a red laser). The skilled artisan will appreciate that the interchangeability of one or more lasers 110 permits the user to begin with a base flow cytometer system and add additional or different lasers 110 as experiments dictate such need. It is possible that during such interchange or exchange of one or more lasers 100, the corresponding beam shaping optics 120 may be changed or adjusted to achieve the optimal delivery of the laser beam at the center of the flow cell 130.

Figure 3:
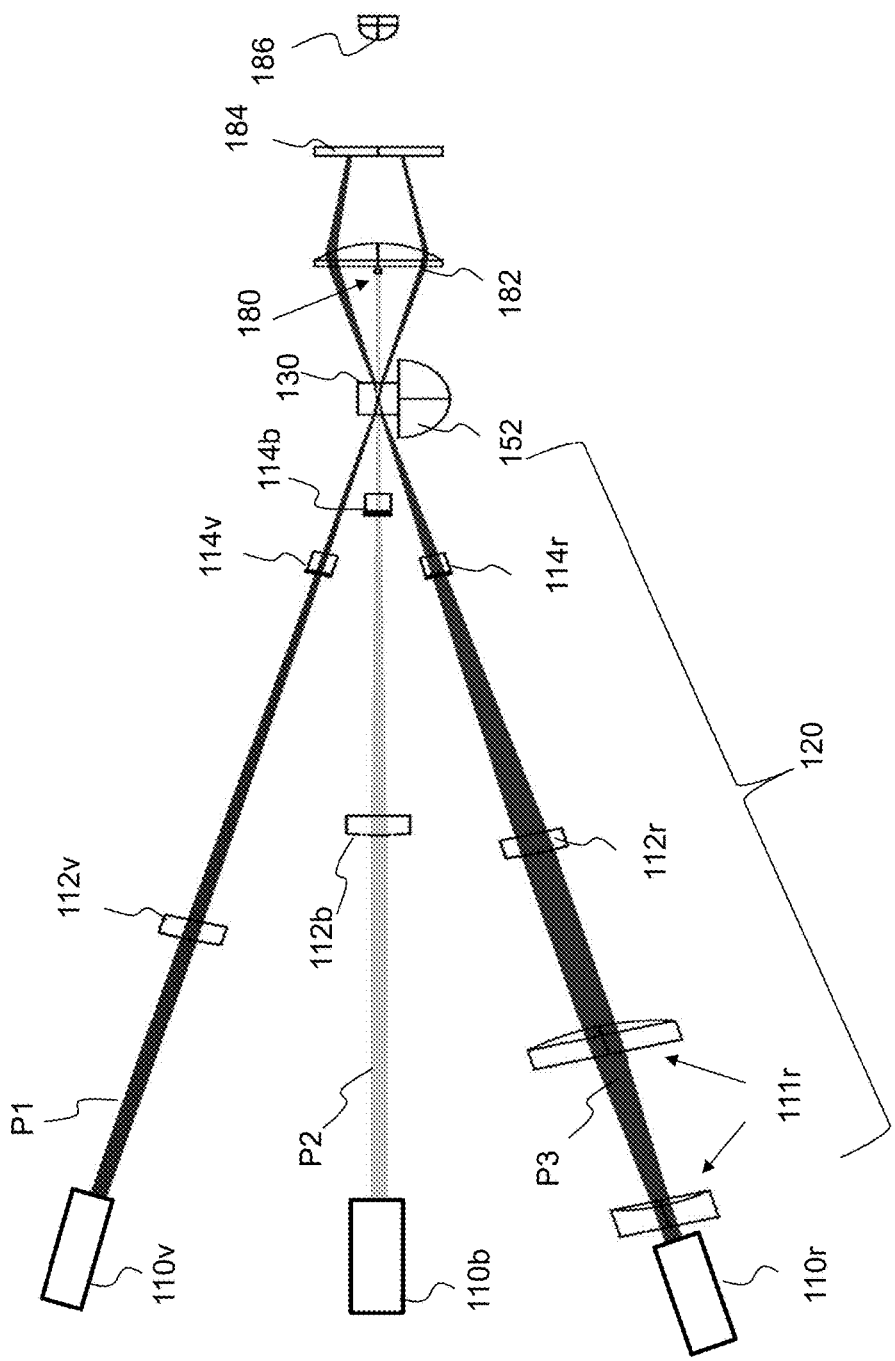
FIG. 3 is a schematic top view of showing laser light propagation along three light paths P1-3 along the Z-axis; wherein horizontal X-axis is normal to the direction of laser light propagation (i.e. Z-axis) of an optical illumination system including 3-laser excitation sources. Also shown is the blocking of unscattered light from path P2 by the obscuration bar 180.

FIG. 3 provides a simplified schematic of a top view showing beam shaping optics 120 for three exemplary optical paths (P1, P2, P3) of three laser beams from the three lasers (e.g. 110v, 110b, 110r), where a first cylindrical lens 112v for the first laser 110v (e.g. 405 nm) focuses excitation light along an X-axis and a second cylindrical lens 114v focuses the excitation light from the first laser 110v along the Y-axis. Similarly, a first cylindrical lens 112b for a second laser 114b (e.g. 488 nm), focuses the excitation light along an X-axis and a second cylindrical lens 114b focuses the excitation light along a Y-axis. A set of two beam expanding lenses 111r expand excitation light from the third laser 110r (e.g. 640), followed by a first cylindrical lens 112r focusing the excitation light along an X-axis and a second cylindrical lens 114r for focusing the excitation light along a Y-axis. The light paths P1, P2, P3 from each laser 110 are focused to a single flow cell 130, through which cells are hydrodynamically focused into a narrow stream in the central region of a flowing sheath fluid.

Also shown is a half-ball lens 152 for collecting fluorescent light and side scatter light emitted from fluorescently labeled cells while travelling through the flow cell 130. An obscuration bar 180 is also shown, which blocks a raw laser beam passing from P2 through the flow cell 130 and towards the forward scatter (FSC) focusing lens 182, which itself focuses FSC light from the second laser 110b (e.g. 488 nm) through a band-pass filter 184 (488/10 nm) for detection by a photodiode 186, which receives the FSC light and converts it to an electrical signal for data acquisition.

Figure 4:
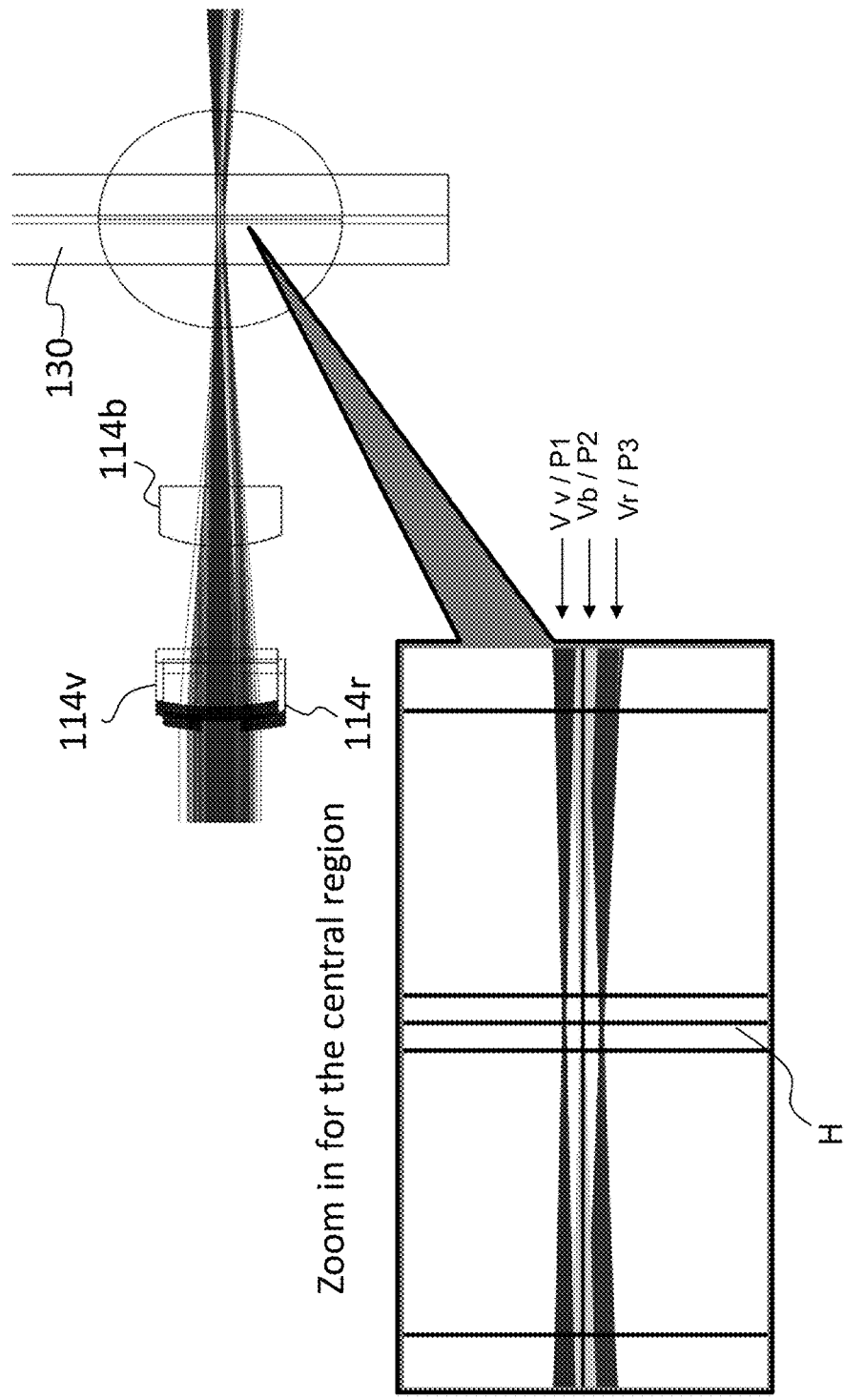
FIG. 4 is schematic depicting an enlarged view of the flow cell 130 showing a common horizontal focus position H for the three light paths P1-P3 and the different vertical focusing positions Vv, Vb, Vr of each path P1, P2, P3.

FIG. 4 is an enlarged schematic showing the three light paths (P1, P2, P3) directed through the corresponding second lens 114v, 114b, 114r converging at a common/same focusing position H (a centerline) along the flow cell 130 but focusing the laser beams at different vertical positions Vv, Vb, Vr along the flow cell 130. As a nonlimiting example, differential vertical focusing can be accomplished by adjusting the second cylindrical lens 114v, 114b, 114r to direct one beam above and one beam below a center beam. For example, the configuration shown in FIG. 3 vertically focuses Vv the first light path P1 from the first laser 110v upwards, by a given distance, (e.g. 80 µm) relative to the vertical focusing positioning Vb of the light path P2 via the second cylindrical lens 114b from the second laser 110b. This results in vertical focusing Vv of the first laser beam/light path P1 in the flow cell 130 vertically above the vertical focusing Vb of the second light path P2 by a same distance, (e.g. 80 µm). Similarly, adjusting the second cylindrical lens 114r for the third laser 110r downwards by a given distance (e.g. 80 µm) relative to the vertical position Vb of the second cylindrical lens 114b for the second laser 110b results in the vertical focusing Vr of the third laser beam P3 in the flow cell 130 vertically lower by the same distance (e.g. 80 µm) relative to the second laser beam P2. The skilled artisan will appreciate that while this separation is depicted 80 µm apart, separations more or less than these could be performed. In some embodiments the beams P1-P3 are separated from neighboring beams P1-P3 by 70 µm. In other embodiments, separation is 50 µm, 55 µm, 60 µm, 65 µm, 75 µm, 85 µm, 90 µm, 100 µm, 125 µm, 150 µm, 175 µm, or 200 µm. Furthermore, adjusting the Z-axis positions of the three above-mentioned second cylindrical lenses 114v, 114b, 114r allows the three laser beam's Z-axis focal points coincide with the center line in the flow cell 130, thus leading to the coincidence of laser beams' Z-axis focal points within the focused sample narrow stream. By focusing at different vertical positions Vv, Vb, Vr along a flow cell 130, the fluorescence signals emitted by a particle traveling through three focused laser beams at different vertical positions is then collected by collection optics, filtered to different wavelength ranges according to filtration optics, and can be further separated into different locations on a same plane within a couple of mm to a few mm distances between neighboring beams according to laser sources by which fluorescence is excited.

Referring collectively to FIGS. 1-4, there are unique advantages for independently controlling three separate optical paths P1, P2, P3 from three lasers 110v, 110b, 110r. First, it is straightforward to separately adjust the alignment of each focused beam along the X-axis to the hydrodynamically-focused sample stream, by adjusting the X-axis position of first cylindrical lens 112. This can be used to eliminate interference between different laser beams and between different optical paths P1, P2, P3, thus allowing each laser beam to be adjusted to optimal alignment.

Secondly, one can independently adjust the Z-axis positions of the second cylindrical lens 114 for each laser beam, ensuring the coincidence or alignment of the focal plane for the Y-axis beam with the hydrodynamically-focused fluid stream in the flow cell 130. Again, there is no interference between different laser beams and between different optical paths P1, P2, P3, thus allowing each laser beam to be adjusted to the optimal alignment with the fluidics.

Thirdly, one can readily adjust and control the separation distance along the Y-axis between three different beams in the flow cell 130, by simply adjusting and moving the height of the second cylindrical lens 114 along the Y-axis for each laser beam. With such an approach, one could adjust the beam separation distance continuously over a relatively-large range.

Fourthly, by providing separate beam shaping and beam guidance optics for each laser independently of the others, one could choose or use lasers 110 having the same or different raw beam diameters, since for each channel different cylindrical lenses 112, 114 could be used with different focal lengths to accommodate the difference in the raw beam diameters.

Fifthly, such an optical illumination design would allow easy configuration and possible upgrade of the laser illumination sources. For example, one could start with a system having a single laser 110 as excitation source. When there is a need for providing additional laser 110 sources of different wavelengths, the new laser(s) 110, together with its (their) corresponding beam shaping and guidance optical components 120, could be readily added to the system, without affecting the existing laser 110 and its beam shaping optics 120. These unique advantages would allow optimal alignment and focus of each laser beam in the flow cell 130, overcoming the limitations compared to other light illumination designs where different lasers share the same optical path for beam shaping and beam separation, and focus and alignment for different lasers need to be compromised.

Forward light scatter (also referred to as forward scatter or low angle scatter) refers to the measurement in flow cytometry that involves light refracted forward due to the passing of a cell through a laser beam and is roughly proportional to the diameter of the cell. When no cell is passing through the path of the laser beam the beam passes uninterrupted through the flow cell 130 and is blocked by an obscuration bar 180 so that no light from the laser beam itself would arrive in the detector. However, when a cell passes through the flow cell 130, light is refracted in all directions. The light refracted in the forward direction misses the obscuration bar 180 to reach the forward scatter detector 186.

In U.S. Pat. No. 9,575,063, herein incorporated by reference in its entirety, we described the development of novel light obscuration bar. To this end, the methods, devices and systems herein preferably include a light obscuration bar 180, such as those described in U.S. Pat. No. 9,575,063. In a preferred embodiment, a diamond shaped obscuration bar 180 is provided. In another embodiment an obscuration bar 180 that is of a rectangular shape and has its horizontal dimension being the same as or longer than its vertical dimension is provided for blocking the incident laser beam. In still another embodiment, the perimeter of the obscuration bar 180 follows a contour of a light intensity distribution plot for blocking incident laser beam. In a still further embodiment, the obscuration bar 180 follows a contour of a light intensity distribution plot within the 0.1% contour line. A 0.1% contour line or boundary corresponds to a line where the light intensity at each point on the contour is at 0.1% of maximum light intensity of the incident light. An obscuration bar 180 following the contour of a light intensity distribution plot within the 0.1% contour was determined to block 99% of the unscattered beam from the FSC detector. Accordingly, the invention also provides an obscuration bar 180 generally diamond shaped that follows a contour of a light intensity distribution plot within the 0.1%, 0.2%. 0.5%, 1.0% or 2.0% contour line and methods of its shaping.

Flow cytometry conventionally includes the labeling of cells with one or more fluorophores. This is typically performed by adding a fluorescently labeled reagent, such as a fluorescently labeled antibody against a surface marker, to a suspension of cells, then washing away unbound reagent. Fluorophores present on or in the cell as it passes through the laser beam adds to the cumulative signal from the cell. Such reagents are well known in the art and available from many suppliers. Both side scatter and fluorescence are collected through collection optics 150 positioned generally orthogonal to the laser beam path then filtered and reflected into different channels using filtration optics 140, such as dichroic mirrors. Dichroic mirrors permit passage of a certain wavelength ranges and reflect the remaining wavelengths.

In the context of the present invention, the flow cytometer 10 incorporates an optical engine 100, including: a set of lasers 110, each emitting light at a specific wavelength suited for excitation of fluorescent molecules; where lights from lasers are focused horizontally along an x-axis to a same horizontal position H and focused vertically along a y-axis to a different vertical position Vv, Vb, Vr along a same excitation plane, wherein the plane is characterized as a flow path through a flow cell 130 of the flow cytometer 10; a set of optics, which includes collection optics 150 for collecting particle-scattered light and fluorescence from the flow cell, and filtration optics 140 that filter the collected fluorescence from the flow cell 130 into different wavelength ranges, wherein the set optics further separate the fluorescence of a same wavelength range into different locations in a focal plane of the collection optics according to the different lasers 110 by which the fluorescent light is excited; and a detector 160 that selectively detects light at the different locations, thereby distinguishing between fluorescence emitted within the same wavelength range from different lasers 110v, 110b and 110r within the set of lasers 110 and converts light to an electrical signal. The preferred embodiment of optical detectors 160 in the present invention are embodied as MPPC detectors 160. Each fluorescent or measurement channel among a plurality of channels can therefore be characterized as belonging to a wavelength range emitted using a single laser 110v, 110b, 110r from the set of lasers 110. To this end, a plurality of channels provide a plurality of data sets for sample analysis.

Figure 5:
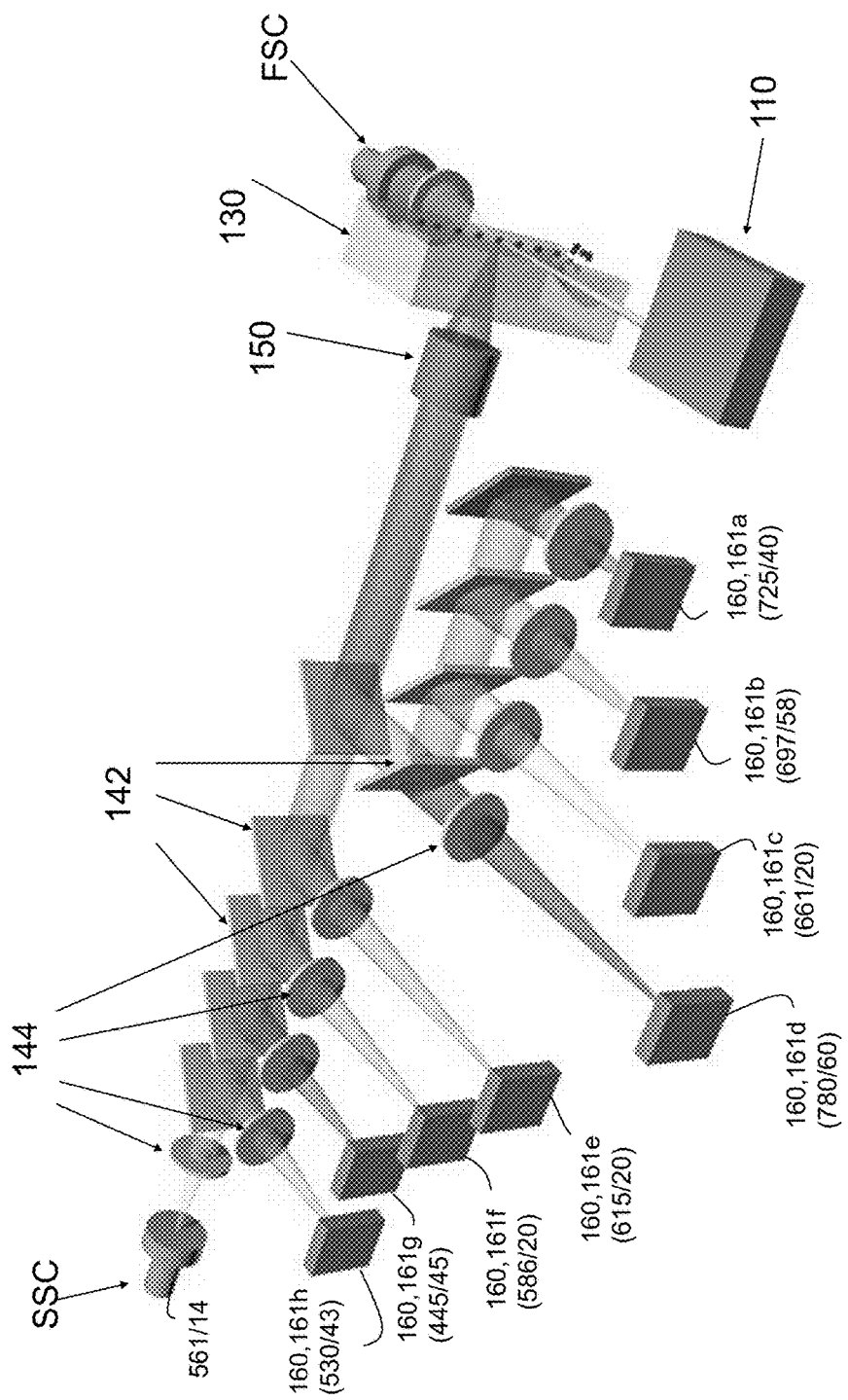
FIG. 5 is a schematic showing the splitting of collected light from a flow channel in a flow cell into six different fluorescent wavelength ranges plus one side scatter channel (SSC). Using apparatus and methods in the present invention, the six fluorescent wavelength ranges could correspond to 13 fluorescent color channels.

A more detailed overview is shown in FIG. 5, where fluorescence and SSC signals from a flow cell 130 are collected using collection optics 150 then split into different detection channels with filtering optics 140, primarily comprised of long pass and/or short pass dichroic mirrors 142 and bandpass filters 144. Shown are a number of MPPC modules (161*a*-161*h*) for the detection of the following fluorescent wavelength ranges: 725/40 nm (161*a*), 697/58 nm (161*b*), 661/20 nm (161*c*), 780/60 nm (161*d*), 615/20 nm (161*e*), 586/20 nm (161*f*), 445/45 (161*g*), 530/43 (161*h*). Each MPPC module 161*a-h* comprises at least one MPPC detector 160, for converting optical light signal to electronic signals. The MPPC detectors 160 are further electrically connected to circuitry (not shown for simplicity) for analog to digital conversion, and the converted digital signals are then be processed by microprocessors that are in communication with a computer (also not shown). Further, TABLE 1 provides a nonlimiting listing of compatible fluorophores for conducting 21 color (or 21 channel) flow cytometry analysis, when each MPPC detector could be used to derive fluorescence signal from different lasers. To this end, each channel within the 21 channel flow cytometry system is characterized by a particular originating laser and a wavelength range.

TABLE 1

| | Excitation | 445/45 | 530/43 | 586/20 | 615/20 | 661/20 | 697/58 | 725/40 | 780/60 |
|---|---|---|---|---|---|---|---|---|---|
| Pacific Blue | 405 nm | X | | | | | | | |
| BV 421 | 405 nm | X | | | | | | | |
| DAPI | 405 nm | X | | | | | | | |
| BV510 | 405 nm | | X | | | | | | |
| AmCyan | 405 nm | | X | | | | | | |
| PACIFIC ORANGE | 405 nm | | | X | | | | | |
| BV605 | 405 nm | | | | X | | | | |
| QDOT 605 | 405 nm | | | | X | | | | |
| BV650 | 405 nm | | | | | X | | | |
| QDOT 655 | 405 nm | | | | | X | | | |
| BV711 | | | | | | | | X | |
| QDOT 705 | 405 nm | | | | | | | X | |
| BV786 | | | | | | | | | X |
| QDOT 800 | 405 nm | | | | | | | | X |

TABLE 1-continued

| | Excitation | 445/45 | 530/43 | 586/20 | 615/20 | 661/20 | 697/58 | 725/40 | 780/60 |
|---|---|---|---|---|---|---|---|---|---|
| Fluoroscein | 488 nm | | X | | | | | | |
| FITC | 488 nm | | X | | | | | | |
| ALEXA FLUOR 488 | 488 nm | | X | | | | | | |
| GFP | 488 nm | | X | | | | | | |
| PE | 488 nm | | | X | | | | | |
| PE-CY 5 | 488 nm | | | X | | | | | |
| PERCP | 488 nm | | | | | X | | | |
| 7-AAD | 488 nm | | | | | X | | | |
| PERCP-CY5.5 | | | | | | | X | | |
| PERCP-eFluor710 | 488 nm | | | | | | | X | |
| PE | 561 nm | | | X | | | | | |
| PE-Texas Red | 561 nm | | | | X | | | | |
| PE-Cy5 | 561 nm | | | | | X | | | |
| PE-Cy5.5 | 561 nm | | | | | | X | | |
| PE-Cy7 | 561 nm | | | | | | | | X |
| APC | 640 nm | | | | | X | | | |
| ALEXA FLUOR 680 | 640 nm | | | | | | X | | |
| ALEXA FLUOR 700 | 640 nm | | | | | | | X | |
| APC-CY 7 | 640 nm | | | | | | | | X |

By focusing excitation laser beams at distinct vertical positions along the flow cell 130 and collecting light from the flow cell 130, the light from each of the vertical positions is collected and split into different wavelength ranges, such as shown in FIG. 5. Furthermore, the light from each of the vertical positions, when collected and filtered down through the filtration optics, was separated to about a couple millimeters to a few millimeters between neighboring beams, according to the laser source by which the fluorescence light is excited.

Figure 6A:
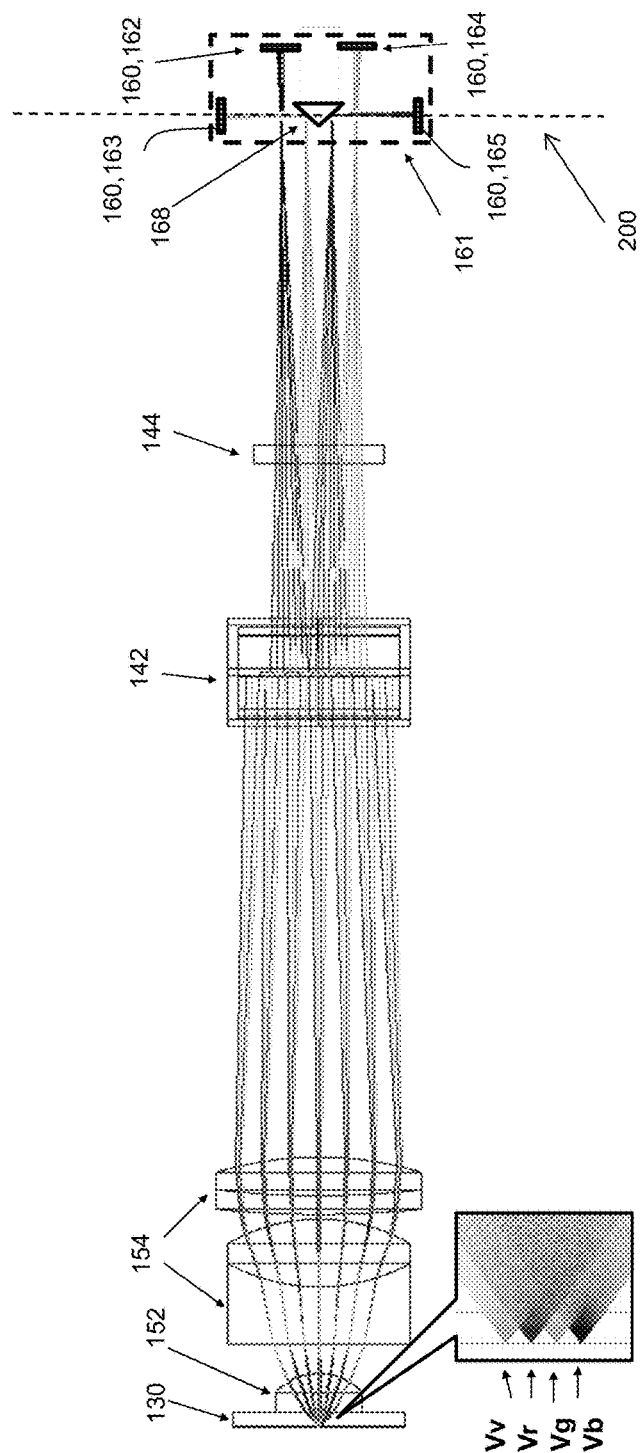
FIG. 6A is a schematic showing fluorescent light from four different vertical positions (Vv, Vr, Vg, Vb) from a same flow cell 130 collected by collection optics 152, 154, traveling through light splitting module 142, filtered by a band-pass filter 144, focused at focal plane 200 of collection optics 152, 154, and detected within detection module 161 having detectors 162-165.

A more detailed schematic of the collection and measurement of spatially distinct positions in a flow cell is shown in FIG. 6A. In this exemplary embodiment, fluorescence from four distinct vertical positions (Vv, Vr, Vg, Vb) along a flow cell 130 is collected using a high refractive index half ball lens 152 (for example, n is about 1.5 or above). The optical path of each proceeds through two sets of doublet lenses 154 (with a large NA>0.8 or above) for collimating fluorescent light and filtered through one or more dichroic mirrors 142. As already eluded to, the half-ball lens 152 is preferably made of high refractive index materials. Such a choice is for maximize the Numerical Aperture (N.A.) and for reducing the overall diameter/size of the fluorescent light beam following the half-ball lens 152. This reduced beam diameter also permits a smaller diameter for the doublet lens 154, making the design and manufacturing of such a doublet lens 154 somewhat less-difficult. It has been found that the combination of high refractive index half-ball lens 152 and doublet lenses 154 results in a high numerical-aperture objective for collecting fluorescent light efficiently. Such a design not only results in a high collection efficiency but also leads to a reduced cost for design and manufacturing of such objectives. The optical path then proceeds through a bandpass filter 144, and to an MPPC module 161.

As illustrated in FIG. 6A, light from each of the distinct vertical positions Vv, Vr, Vg, Vb is focused to a small beam size (for example, about a couple of millimeters or less) with a separation distance of a couple of millimeters to a few millimeters between neighboring beams as light is collected through collection optics (halfball lens 152, two sets of doublet lenses 154) and travels through the filtration optics (dichroic mirror 142, bandpass filter 144), reaching the MPPC detection module 161. At a focal plane 200 of the collection optics (halfball lens 152, two sets of doublet lenses 154), adjacent beams of a same wavelength range are spaced a couple to a few millimeters apart. To be clear, in this case, the collection optics comprising halfball lens 152 and two sets of doublet lenses 154 collects scattered light and fluorescent light from different locations (Vv, Vr, Vg, Vb) of the follow cell and focus the light onto a focal plane 200 where each focused beam size is, generally, less than 500 microns in diameter. For the example shown in FIG. 6A, the MMPC module 161 includes a prism mirror 168 that further separates apart the light from the two middle vertical positions in the flow cell 130 so that each light beam is detected independently through a MPPC detector 162, 163, 164, 165. Note in one particular embodiment, the focal plane 200 coincides with the mirror-reflection points of the prism mirror 168. In FIG. 6A, Total 4 detectors 162, 163, 164 and 165 are used to detect fluorescence light from the four distinct vertical positions Vv, Vr, Vg, Vb in the flow cell 130, as excited each individual laser.

In a preferred embodiment, each light beam goes through a lens for expanding the beam before reaching an MPPC detector. This is shown in FIG. 6B. The light beams from four different vertical positions Vv, Vr, Vg, Vb in the flow cell 130 travel through different optical components within the set of optics before reaching MPPC detector surfaces in the following manner. Similar to FIG. 6A, the light from the two middle vertical positions Vr, Vg in the flow cell 130 is further separated apart by the prism mirror 168. The light reflected by the upper surface of the prism 168 reaches the reflection mirror 172, then goes through a lens 193 before reaching the surface of MPPC detector 163 for detection. Similarly, the light reflected by the lower surface of the prism 168 reaches the reflection mirror 174, then goes through a lens 195 before reaching the surface of MPPC detector 165. The light from the top vertical positions Vv in the flow cell 130 goes through a lens 192 and reaches the surface of MPPC detector 162 for detection. The light from the lowest vertical positions Vb in the flow cell 130 goes through a lens 194 and reaches the surface of MPPC detector 164 for detection. The use of the lenses 192, 193, 194 and 195 expands the beams to an improved size for detection at MPPC surfaces (a consistent and optimized beam size is possible through the design and the use of the lenses 192, 193, 194 and 195). In addition, the lenses 192, 193, 194 and 195 serve an additional design function of resulting a uniform beam distribution at MPPC surfaces. Such an optimized beam size and beam uniformity (through the design of the lenses 192, 193, 194 and 194) helps the improvement of linear-dynamic detection range of MPPC devices being used for light detection here.

An additional important feature of the present invention is a multi-pixel photon counter (MPPC) chip to detect fluorescent light. Comparing with PMTs widely used in flow cytometry, MPPC presents some distinguishing features such as smaller foot print in size and larger quantum efficiency, allowing the measurement of low light signals. Whilst MPPCs could theoretically be used in flow cytometry to detect and measure fluorescent light, it has not been used in practical cytometers, for a number of reasons such as a large dark-count background, the gain being temperature dependent, and possibly limited dynamic range.

To this end, in another embodiment of the present invention, an optical engine for use in a bench top flow cytometer is provided, which includes, a laser, tuned to a wavelength suited for excitation of fluorescent molecules, wherein light from the laser is focused horizontally along an x-axis to a horizontal position and vertically along a y-axis to a vertical position along an excitation plane, wherein the horizontal position along the excitation plane intersects a flow path through a flow cell of a flow cytometer; a set of optics comprising collection optics for collecting fluorescence emitted from the flow cell and filtration optics that filter the collected fluorescence from the flow cell into different wavelength ranges, thereby providing different fluorescent channels; and an MPPC detector at each fluorescent channel to detect fluorescence and convert light to an electrical signal. In a preferred embodiment, the optical engine further comprises a set of lasers, wherein each of the lasers is focused vertically along the y-axis to a different vertical position along the same excitation plane, further wherein the set of optics separate the emitted fluorescence from the flow cell into different fluorescence channels, wherein each channel is characterized by a different wavelength range and a different laser by which the fluorescence is excited.

In preferred embodiments of above optical engines, the MPPC is operated with a linear dynamic range above 3 decade. More preferably, the MPPC is operated with a linear dynamic range above 4 decade.

In some embodiments of above optical engines, the MPPC digital output value is corrected according calibration factors. Preferably, the calibration factors improve linear dynamic range of the MPPC by more than half decade. More preferably, the calibration factors improve linear dynamic range of the MPPC by more than one decade. Even more preferably, the calibration factors improve linear dynamic range of the MPPC by more than one and one-half decade. Still, even more preferably, the calibration factors improve linear dynamic range of the MPPC by more than two decades.

In a preferred embodiment, forward scatter (FSC) characterization of cells includes a FSC detector, a FSC focusing lens to collect FSC light, and an obscuration bar that blocks an incident laser beam from entering the FSC focusing lens and the FSC detector. The relationship between timing of fluorescence signal at a fluorescent light detector and timing of forward scatter signal at a FSC detector provides an approach for determining which laser induces excitation of a detected fluorescent signal in a detection channel.

Further improvement of forward scatter (FSC) detection has been achieved through the use of improved obscuration bars. In a preferred embodiment, a diamond shaped obscuration bar is provided. In another embodiment an obscuration bar that is of a rectangular shape and has its horizontal dimension being the same as or longer than its vertical dimension is provided for blocking the incident laser beam. In still another embodiment, the perimeter of the obscuration bar follows a contour of a light intensity distribution plot for blocking incident laser beam. In a still further embodiment, the obscuration bar follows a contour of a light intensity distribution plot within the 0.1% contour line. A 0.1% contour line or boundary corresponds to a line where the light intensity at each point on the contour is at 0.1% of maximum light intensity of the incident light. An obscuration bar following the contour of a light intensity distribution plot within the 0.1% contour was determined to block 99% of the unscattered beam from the FSC detector. Accordingly, the invention also provides an obscuration bar generally diamond shaped that follows a contour of a light intensity distribution plot within the 0.1%, 0.2%. 0.5%, 1.0% or 2.0% contour line and methods of its shaping.

Components of the optical engine are preferably housed as a single unit, and some of these optical components can be removed and interchanged for modification with other components. To this end, a housing configured to house optical engine components is also provided. The housing includes the optical engine components such as the set of lasers, the optics for focusing laser beams to the excitation plane, collection optics, filtration optics, photo-detectors or light-detectors, further filters (and/or lenses), as well as an electrical interface for electrical connection from the photo-detectors or light-detectors to electrical circuitry, which would be connected to an external microprocessor or a remote computer. In some embodiments, each laser has a corresponding set of beam-shaping optics wherein light from each laser is focused horizontally along an x-axis to a same horizontal position and vertically along a y-axis to a different vertical position along a same excitation plane, wherein the same horizontal position along the excitation plane intersects a flow path through a flow cell of a flow cytometer. In other embodiments, all the laser beams being independently adjustable horizontally along an x-axis and independently adjustable vertically along a y-axis, are combined together via suitably placed dichroic mirrors and go through a common achromatic beam shaping optics so that all the laser beams are focused to a same horizontal position and to different vertical positions along a same excitation plane, wherein the horizontal position on the excitation plane interests a flow path through a flow cell of the flow cytometer. Preferably, the components within a same housing are configured for interchangeability of different lasers, focusing lenses, long pass and short pass dichroic mirrors, filters, pinhole passages and detectors. This is accomplished by standardizing engagement features such as positioning of alignment holes, snaps, screws or other fasteners across different components for interchangeability and by providing a set of beam shaping optics for each laser individually. Preferably, the photo-detectors or the light detectors are MPPC detectors. In some embodiments, a flow channel is mounted in the housing and configured for coupling to a flow cytometer apparatus for hydrodynamic focusing of samples including particles (e.g. beads or cells) by tubing connectors.

Figure 7A:
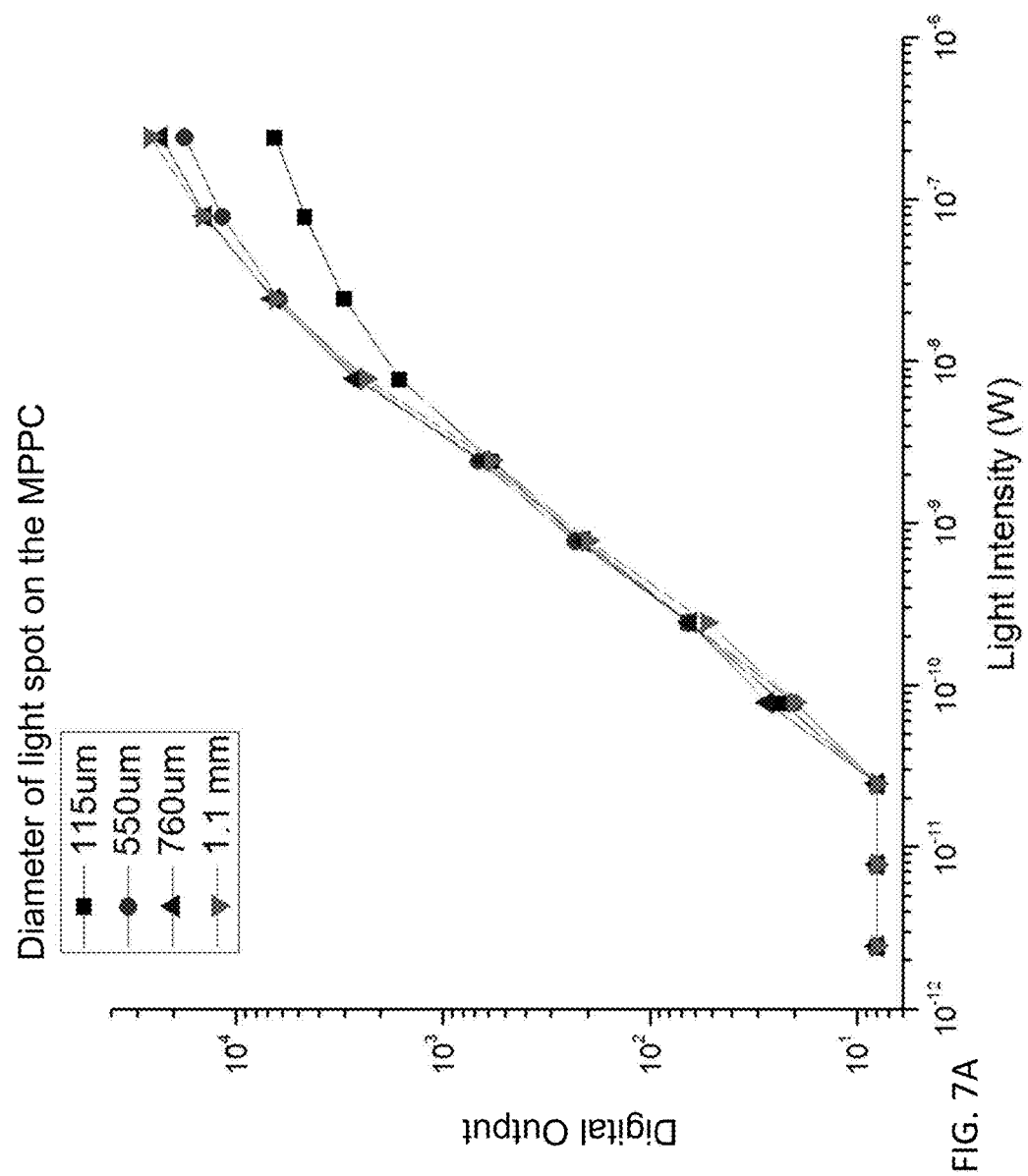
FIG. 7A shows the dependency of the digital output from an MPPC detector of 1.5 mm×1.5 mm in size on the power level of the incident light.

In furtherance of the above embodiments, FIG. 7A shows that the dependency of the digital output after converting electronic analog signals from an MPPC on the power level of the incident light. For this test, the incident light was pulsated at 10 kHz with a pulse duration of 4 µs. The analog electrical current output from MMPC chip is converted to a voltage with a resistor. The voltage is then digitized to give digital output. The incident light beam was varied from about 115 um to 1.1 mm. Clearly, the larger the beam size, the wider the linear dynamic range. For this MPPC chip of about 1.5 mm×1.5 mm in size, out of the beam sizes being evaluated shown in FIG. 7A, 1.1 mm beam size gave the better dynamic ranges than those for beam sizes of 760 um, 550 um and 115 um. The beam size refers to the diameter of light spot for the incident beam on the MPPC surface.

Figure 7B:
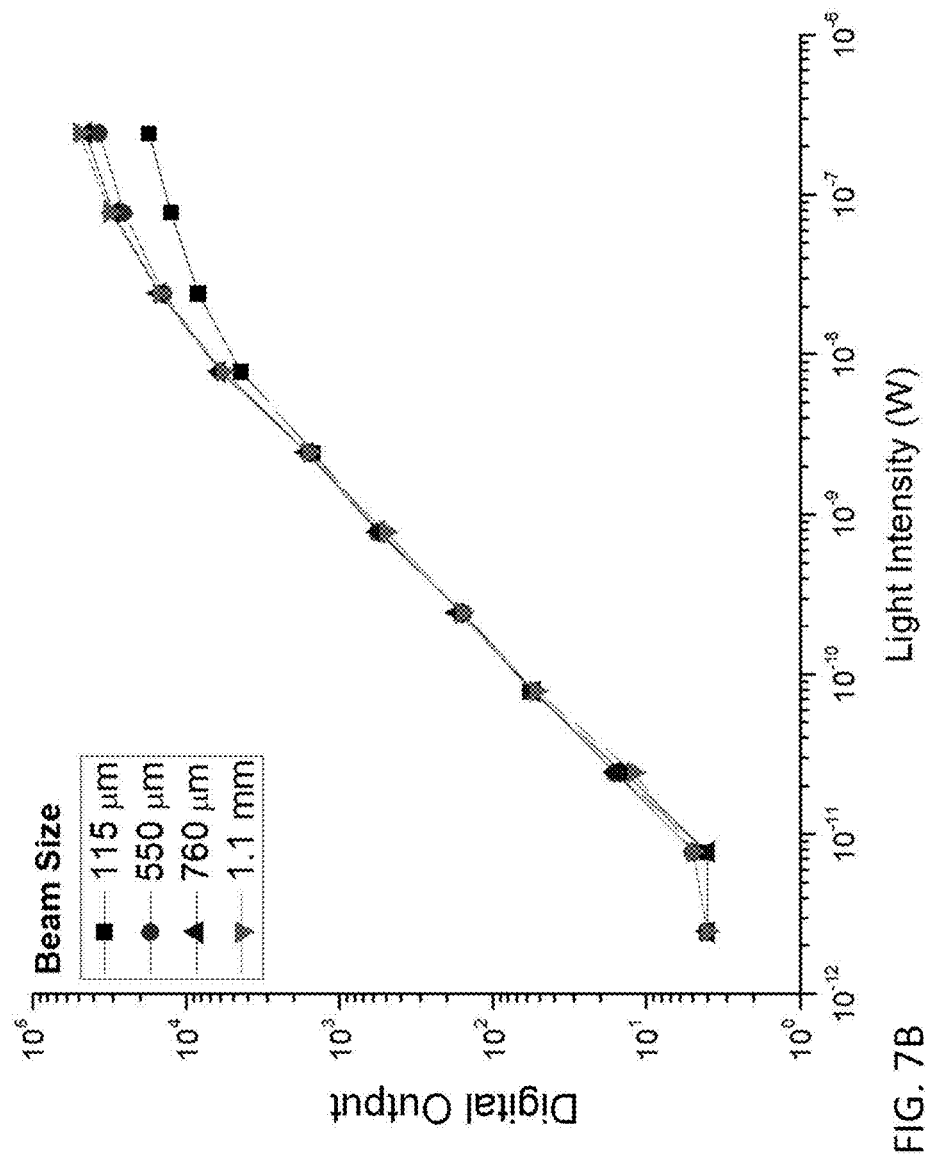
FIG. 7B shows that the dependency of the digital output from another MPPC detector with different resistors from that used in FIG. 7A (the resistors are used for converting MPPC output electric current to electrical voltage).
Figure 7C:
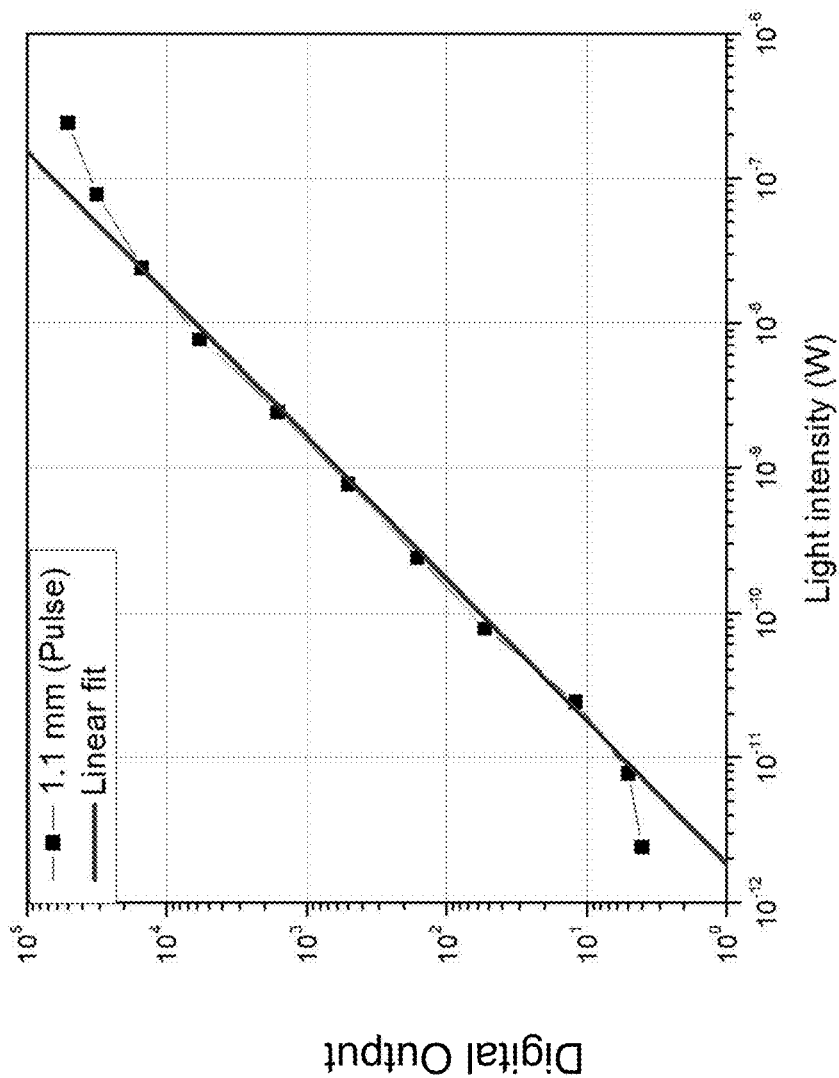
FIG. 7C shows a linear regression fit of MPPC digital output versus incident light intensity for the beam size of 1.1 mm in FIG. 7B.

FIG. 7B shows that the dependency of the digital output from another MPPC detector with different resistors from that used in FIG. 7A. Here the resistors are used for converting MPPC output electric current to an analog electrical voltage, which is further converted to a digital MPPC output with an ADC. The resistors in FIG. 7B are larger than those used in FIG. 7A, as such, the digital output from FIG. 7B is larger than that in FIG. 7A. Similar to the data in FIG. 7A, 1.1 mm beam size gave better dynamic ranges than those for beam sizes of 760 um, 550 um and 115 um. FIG. 7C shows a linear regression fit of MPPC digital output versus incident light intensity for the beam size of 1.1 mm. As evident in FIG. 7C, the MPPC output for the incident beam size shows a linear dynamic range about 3.5 decade. That is to say, for the light intensity between about $10^{-11}$ W to about $3 \times 10^{-8}$ W, the MPPC shows a linear response in terms of the digital output being proportional to the light intensity.

Figure 8:
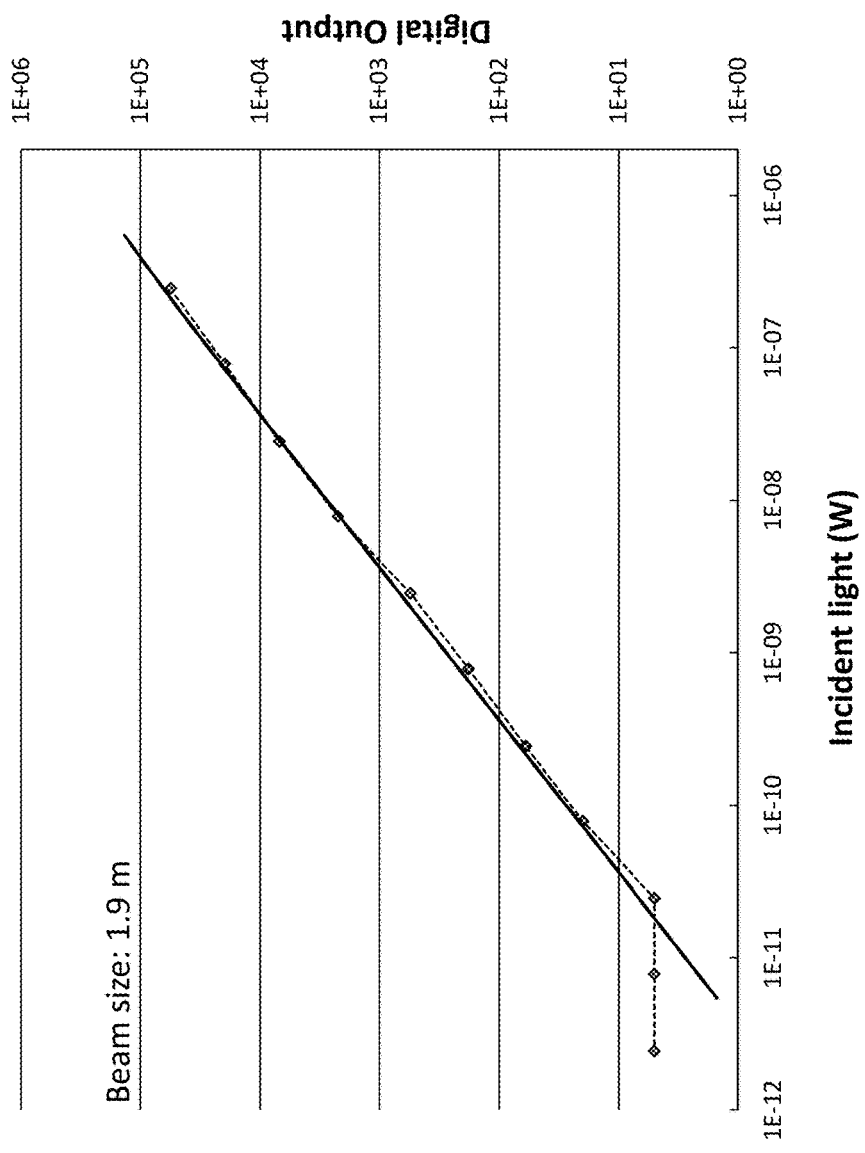
FIG. 8 shows the dependency of the digital output after converting electronic analog voltage signals from an MPPC on the power level of the incident light. The MPPC is of 3 mm×3 mm in size.

FIG. 8 shows that the dependency (diamond symbol on broken line) of the digital output after converting electronic analog voltage signals from an MPPC on the power level of the incident light. For this test, the incident light was pulsated at 10 kHz with a pulse duration of 4 µs. The analog electrical current output from MMPC chip is converted to a voltage with a resistor. The voltage is then digitized to give digital output. The incident light beam was 1.9 mm for this MPPC chip of about 3 mm×3 mm in size. The beam size refers to the diameter of light spot for the incident beam on the MPPC surface. The solid line in FIG. 8 shows a linear regression fit of MPPC digital output versus incident light intensity for the measured MPPC data versus light intensity. As evident in FIG. 8, the MPPC output for the incident beam size shows a linear dynamic range above 4 decade. That is to say, for the light intensity between about $2 \times 10^{-11}$ W to about $3.5 \times 10^{-7}$ W, the MPPC shows a linear response in terms of the digital output being proportional to the light intensity.

Figure 9:
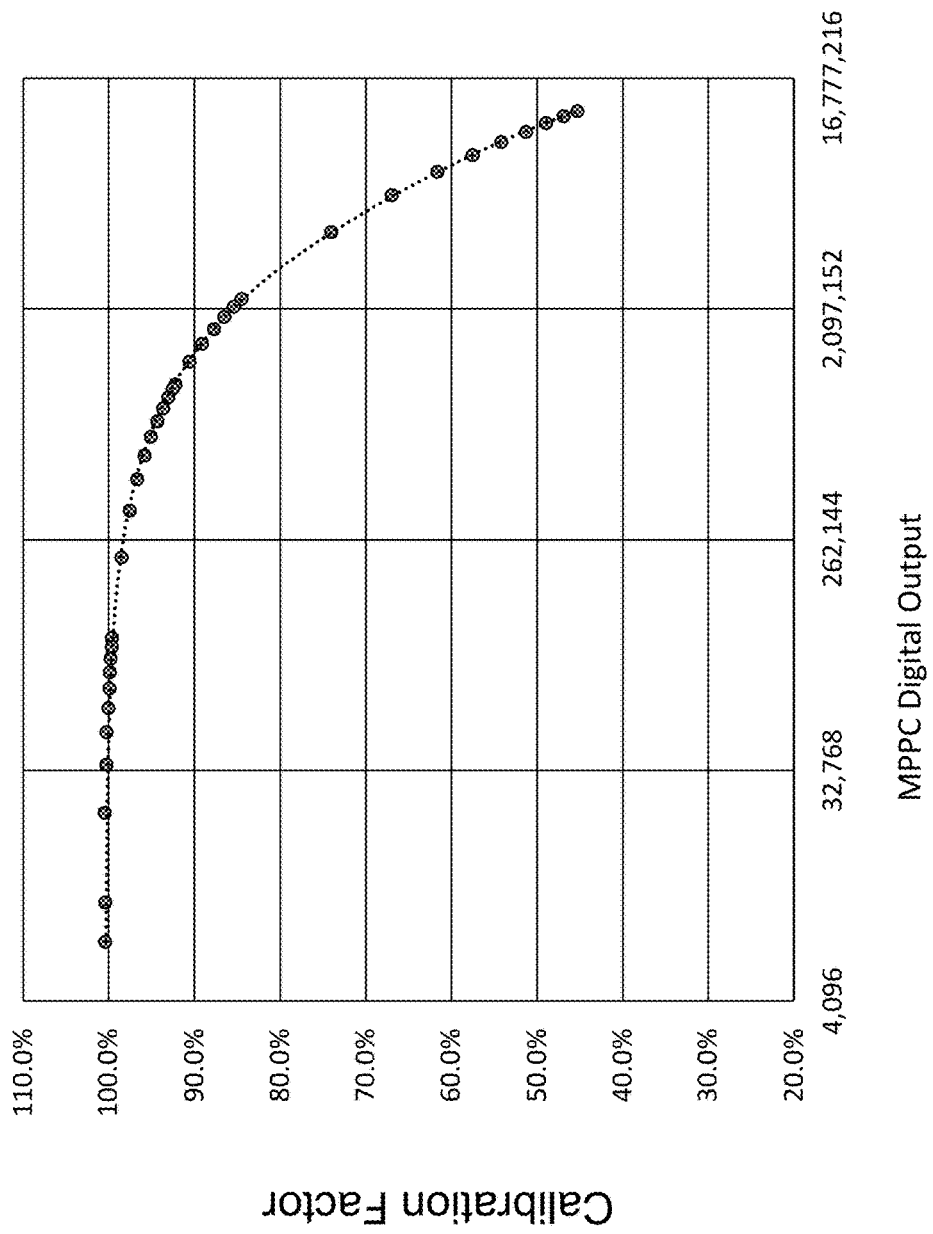
FIG. 9 shows the plot of calibration factor versus MPPC digital output, as determined for an MPPC having size of 3 mm×3 mm in size, at a particular operational bias voltage and room temperature, for incident light beam of wavelength range between 515-545 nm.

FIG. 9 shows the plot of calibration factor versus MPPC digital output, as determined for an MPPC having size of 3 mm×3 mm in size, at a particular operational bias voltage and room temperature, for incident light beam of wavelength range between 515-545 nm. Each calibration factor was determined using the technique described in the above sections of the present invention. Continuous line shows a theoretical modelling of the dependency of the calibration factor on the MPPC digital output using a polynomial equation. This derived equation allows the calculation of calibration factor for any MPPC digital output value. By dividing the MPPC digital output values by corresponding calibration factors, the MPPC output values are corrected and the resulting output data would show significantly improved linearity. The linear dynamic range for the MPPC data showing in FIG. 9 would be improved by more than 1.5 decade when the calibration factors are used to calibrate or correct MPPC digital output values.

Figure 10:
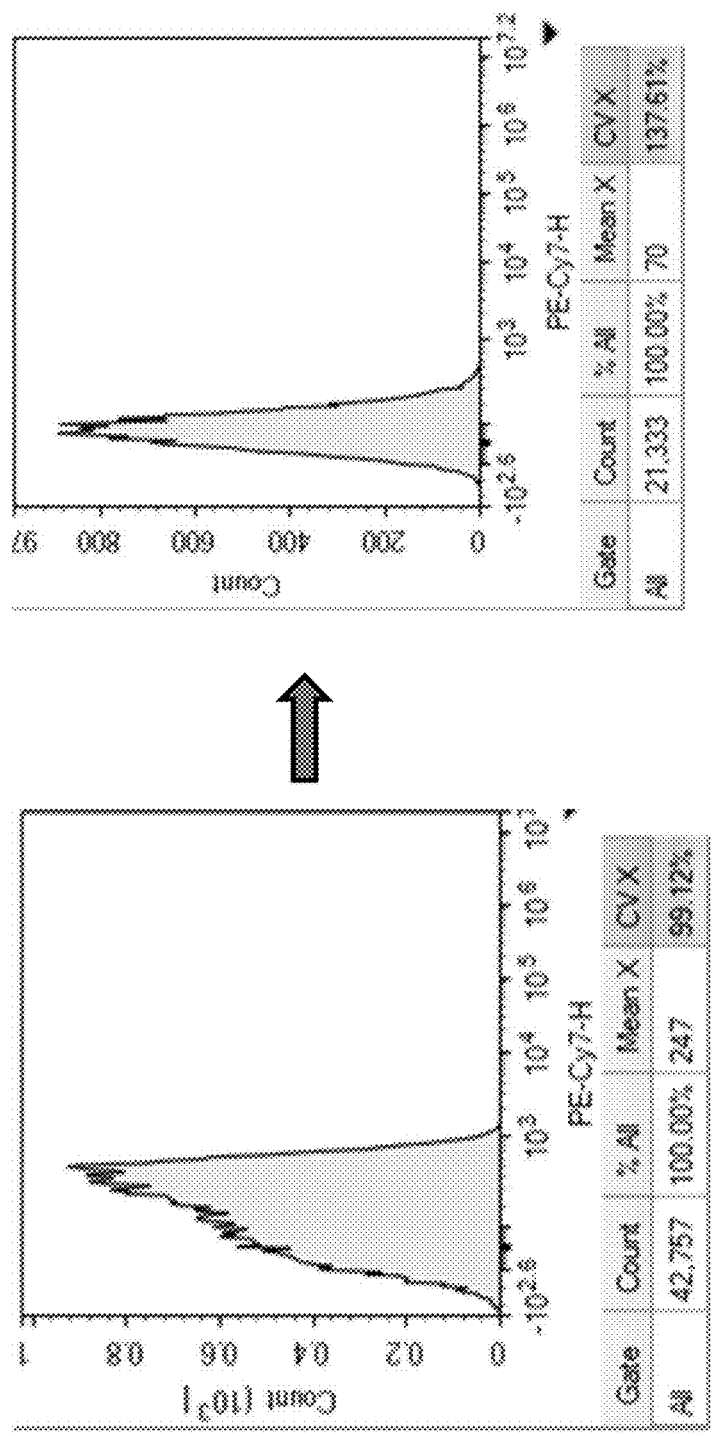
FIG. 10 shows that the histogram of dark count noises with MPPC blocked from any external light with left panel at a room temperature and the right panel at a lowered temperature.

The lower end of the MPPC dynamic range, when the incident light is about a few pW or less, is limited by the optical noises and electronic noises of the system, as well as, very importantly, the dark count of MPPC. In this regard, we have been reducing and controlling the dark-count noise by lowering the operational temperature of MPPCs. FIG. 10 shows that the histogram of dark count noises with MPPC blocked from any external light with left panel at a room temperature and the right panel at a lowered temperature. In this test, MPPC is powered at certain operational voltages. The output 'dark-count' noises in electrical current were converted into a voltage through a resistor. The output voltage is then digitized through an analog-to-digital convertor. The digital output is then processed through algorithm identifying a max value within each small time interval during entire experiment process. This way, each time interval would lead one output value from MPPC circuit. The output values are then plotted in a histogram format. Clearly, the larger the mean for the histogram, the larger the dark count noises. As the temperature for the MPPC chip was reduced, there was a significant reduction in the mean of the distribution of MPPC dark-count output from a digital value of 247 to 70, an about 70% reduction.

Thus, we have shown that reducing the MPPC temperature could reduce the dark count noises. We are now developing special techniques and approaches to lower down the operational temperature of the MPPC.

Figure 11:
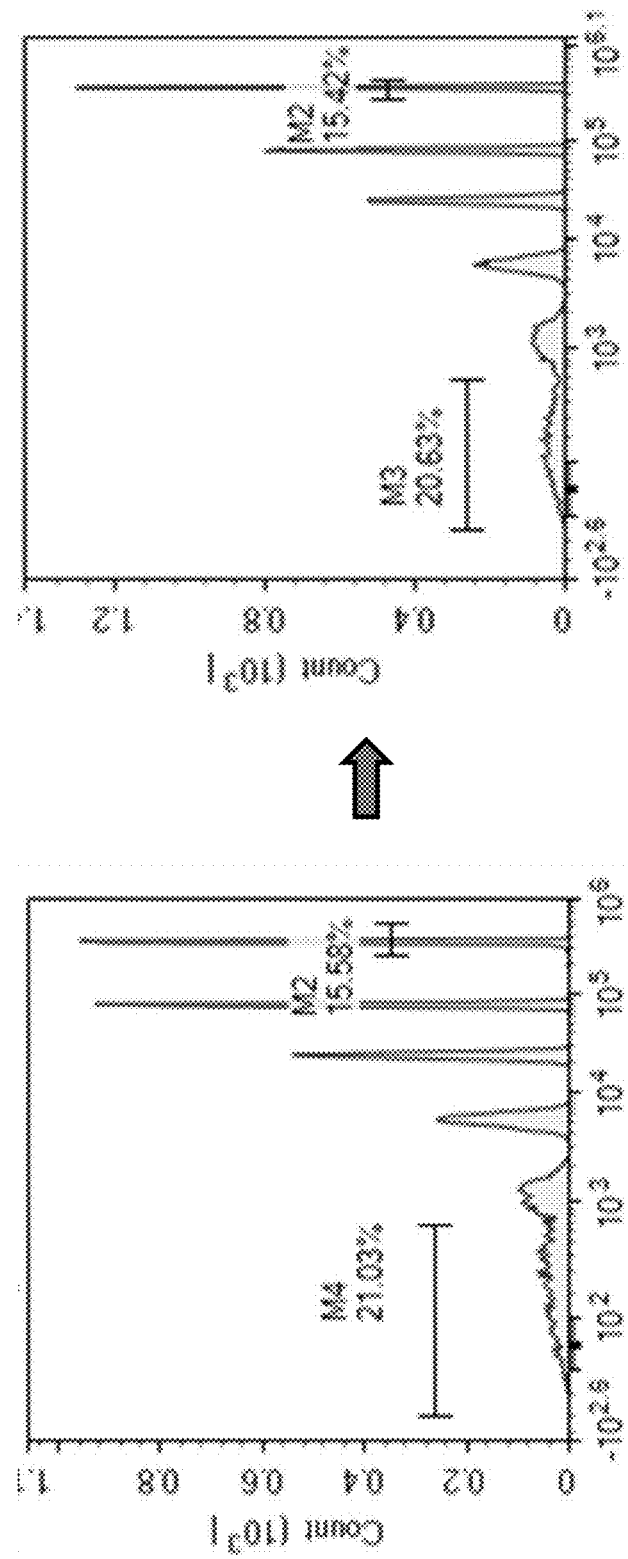
FIG. 11 shows a preliminary data of 6-pk beads detected at the fluorescent channel of 530/43 nm, excite by a blue laser, by a MPPC detector, with left panel at a room temperature and the right panel at a lowered temperature.

FIG. 11 shows a preliminary data of 6-pk beads detected at the fluorescent channel of 530/43 nm, excite by a blue laser, by a MPPC detector, with left panel at a room temperature and the right panel at a lowered temperature. In this test, MPPC is powered at certain operational voltages. The 6-pk beads were running through the flow channel in a flow cell, where laser beams of 488 nm, 640 nm and 405 nm were focused into a same horizontal position and each to a different vertical position separated by 80 um in the center of the flow cell. The fluorescence generated by the beads as they were excited by laser beam were collected through a collection optics and filtered into a wavelength range of about 530 nm/43 nm. The fluorescence due to the blue laser was then detected with a MPPC chip. Clearly, at room temperature showing on the left panel, the detector can barely distinguish two dimmest beads. Yet with reducing the temperature on the right panel, the MPPC detector can readily resolve the two dimmest populations. This clearly illustrates that reducing the operation temperature could improve the system resolution and dynamic range of the fluorescence detection.

Control and communication to the flow cytometer for setup and data acquisition is performed using a computer communicatively coupled to the flow cytometer. Accordingly, flow cytometry software for loading in a computer has also been developed. The flow cytometry software preferably includes data acquisition features and data analysis features. As known in the flow cytometry arts, data acquisition involves the collection and storing of data from an experiment. This may also include set up features for acquiring data, such as compensation adjustment, defining the number of cells to be counted within a particular gated population, setting a sample flow rate, and the other experiment controls encountered in the flow cytometry arts. Data analysis features may include plotting cell subpopulations across one or more fluorescent colors, determining absolute counts for particular cell subpopulations, determining relative percentages of particular subpopulations, cell cycle analysis, as well as other data analysis features found in flow cytometry programs. To this end, the software provides versatile, user friendly and intuitive plotting and gating tools and its statistical tools provide exceptional statistical data analysis capabilities. In preferred embodiments, all acquisition parameters, experiment and sample files, along with plots are visible and accessible in one window area.

In some embodiments, a data collection process can include calculating and processing fluorescence signals of a same wavelength for different detectors into different fluorescence channels (as excited by different lasers, at different vertical positions of an excitation plane); generating a graphical user interface (GUI) that displays two-dimensional plots with one parameter versus another one (e.g. FSC vs. SSC, FSC vs. a fluorescence signal, or one fluorescence signal vs. another fluorescent channel), wherein the GUI further has compensation scroll bars adjacent to the comparison plots to adjust compensation of spectral overlap between one or more channel; collecting data from each light scatter channel and from each fluorescence channel; and saving the data into a data file. The software also preferably includes a gating function that permits the user to select a subpopulation from one of the histogram plots or one of the 2-D plots and generate another plot (which could either be a one-parameter histogram plot or be a two-parameter 2-D plots for the selected subpopulation. This "gating" and further analysis of "gated populations" can be repeated.

In still another related embodiment a flow cytometry method is provided, which includes providing flow cytometer or flow cytometer system as provided herein; labeling a sample of cells with a plurality of fluorescent labels; pumping the sample of cells through the flow channel; collecting flow cytometry data; and analyzing the flow cytometry data to determine the presence, absence or abundance of one or more of the plurality of fluorescent labels on or in cells of the sample.

What is claimed is:

1. An optical engine for use in a bench top flow cytometer, the optical engine comprising:
    a) a set of lasers, each tuned to a wavelength suited for excitation of fluorescent molecules, wherein light from each of the lasers is focused horizontally along an x-axis to a same horizontal position and vertically along a y-axis to a different vertical position along a same excitation plane, wherein the same horizontal position along the excitation plane intersects a flow path through a flow cell of a flow cytometer;
    b) a set of optics comprising collection optics for collecting fluorescence emitted from the flow cell and filtration optics that filter the emitted fluorescence from the flow cell into different wavelength ranges, wherein the set of optics further separate the fluorescence of a same wavelength range into different locations in a focal plane of the collection optics according to the different lasers by which the fluorescent light is excited;
    c) a detector that selectively detects light from the different locations thereby distinguishing between fluorescence emitted within the same wavelength range as excited by different lasers within the set of lasers and converts light to an electrical signal.

2. The optical engine according to claim 1, wherein the set of lasers comprises two, three, four or five individual lasers, each tuned to a different wavelength and directed to a different vertical position of the excitation plane thereby providing two, three, four or five distinct vertical positions along the flow cell respectively.

3. The optical engine according to claim 2, wherein the vertical positions in the flow cell are separated by between 60 and 120 µm.

4. The optical engine according to claim 3, wherein the vertical positions in the flow cell are separated by about 80 µm.

5. The optical engine according to claim 1, wherein the collection optics comprise a half ball lens followed by two sets of doublet lenses.

6. The optical engine according to claim 1, wherein the filtration optics comprise a dichroic mirror or a bandpass filter.

7. The optical engine according to claim 1, wherein the filtration optics filter one or more wavelength ranges selected from the group consisting of 780/60 nm, 615/20 nm, 530/43 nm, 445/45 nm, 586/20, 661/20, 697/58, and 725/40 nm.

8. The optical engine according to claim 1, wherein the different locations in the focal plane of the collection optics are separated from adjacent locations by between 1 millimeter to 4 millimeters, optionally 2 to 3 millimeters.

9. The optical engine according to claim 1, wherein the different locations in the focal plane of the collection optics are spaced 1 to 4 millimeters apart from adjacent locations within the focal plane of the collection optics.

10. The optical engine according to claim 1, wherein the set of optics further comprise a lens for expanding a light beam from each of the different locations in the focal plane of the collection optics to a size of about 1 mm to about 3 mm, wherein each light beam originating from the fluorescence is excited by an individual laser.

11. The optical engine according to claim 1, wherein the detector is multi-pixel photon counter (MPPC) or silicon photomultiplier.

12. The optical engine according to claim 11, wherein the MPPC is operated with a linear dynamic range above 3 decade.

13. The optical engine according to claim 12, wherein the MPPC is operated with a linear dynamic range above 4 decade.

14. The optical engine according to claim 11, wherein the MPPC digital output value is corrected according calibration factors.

15. The optical engine according to claim 14, wherein the calibration factors improve linear dynamic range of the MPPC by more than half decade.

16. The optical engine according to claim 14, wherein the calibration factors improve linear dynamic range of the MPPC by more than one decade.

17. The optical engine according to claim 14, wherein the calibration factors improve linear dynamic range of an MPPC by more than one and half decade.

18. The optical engine according to claim 14, wherein the calibration factors improve linear dynamic range of the MPPC by more than two decades.

19. The optical engine according to claim 1, further comprising a forward scatter (FSC) detector, a FSC focusing lens, and an obscuration bar.

20. The optical engine according to claim 19, wherein the obscuration bar is diamond shaped or has a rectangular shape with its horizontal dimension being the same as or larger than its vertical dimension.

21. The optical engine according to claim 19, wherein a perimeter of the obscuration bar follows a contour of a light intensity distribution plot, optionally within a 0.1% contour line.

22. The optical engine according to claim 21, wherein the obscuration bar blocks 99% of unscattered light from detection by the FSC detector.

23. The optical engine according to claim 1, further comprising a housing configured to house optical engine components, the optical engine components comprising the set of lasers, optics for focusing laser beams to the excitation plane, the collection optics, the filtration optics, and the detector, wherein a same housing is configured for interchangeability of different lasers, lenses, mirrors, filters, and detectors.

24. The optical engine according to claim 1, further comprising the flow cell.

25. A flow cytometer, comprising:
a) the optical engine according to claim 1;
b) a flow cell; and
c) a pump in fluid communication with an aspiration needle for aspirating and delivering a suspension of cells through the flow cell.

26. The flow cytometer according to claim 25, further characterized in that
a) the set of lasers comprises two, three, four or five lasers, each laser tuned to a different wavelength and focused to a different vertical position along the flow cell; and
b) the set of optics spatially distinguishing the filtered fluorescence in the same wavelength range that is excited by each of the two, three, four or five different lasers respectively.

27. A flow cytometry system comprising:
a) the flow cytometer according to claim 25; and
b) a computer operably loaded with developed flow cytometry software to acquire and analyze flow cytometry data.

28. The flow cytometry system according to claim 27, wherein the software provides programming to perform the following functions:
a) acquiring data of fluorescence channels from each detector, wherein the fluorescence signals collected by different detectors are converted to different data series, corresponding to the fluorescence excited by lasers at the different vertical positions;
b) generating a graphical user interface (GUI) that displays various plots for the acquired data, wherein the GUI further comprises compensation scroll bars adjacent to the comparison plots to adjust compensation of spectral overlap between one or more channel; and
c) saving the acquired data into a data file.

29. A flow cytometry method comprising:
a) providing the flow cytometry system according to claim 27;
b) labeling a suspension of cells with a plurality of fluorescent labels;
c) pumping the suspension of cells through the flow channel;
d) collecting flow cytometry data; and
e) analyzing the flow cytometry data to determine the presence, absence or abundance of one or more of the plurality of fluorescent labels on or in cells of the sample.

30. An optical engine for use in a bench top flow cytometer, the optical engine comprising:
a) a laser, tuned to a wavelength suited for excitation of fluorescent molecules, wherein light from the laser is focused horizontally along an x-axis to a horizontal position and vertically along a y-axis to a vertical position along an excitation plane, wherein the horizontal position along the excitation plane intersects a flow path through a flow cell of a flow cytometer;
b) a set of optics comprising collection optics for collecting fluorescence emitted from the flow cell, filtration optics that filter the collected fluorescence from the flow cell into different wavelength ranges, thereby providing different fluorescent channels, and a set of lenses to alter beam size of the fluorescence from the different wavelength ranges; and
c) an MPPC detector configured to receive the altered beam for each fluorescent channel to detect fluorescence and convert light to an electrical signal.

31. The optical engine according to claim 30, further comprising at least 1 to 4 additional lasers, wherein each of the lasers is focused vertically along the y-axis to a different vertical position along the same excitation plane, further wherein the set of optics separate the emitted fluorescence from the flow cell into different fluorescence channels, wherein each channel is characterized by a different wavelength range and a different laser by which the respective fluorescence is excited.

32. The optical engine according to claim 30, wherein the MPPC is operated with a linear dynamic range above 3 decade.

33. The optical engine according to claim 32, wherein the MPPC is operated with a linear dynamic range above 4 decade.

34. The optical engine according to claim 30, wherein the MPPC digital output value is corrected according calibration factors.

35. The optical engine according to claim 34, wherein the calibration factors improve linear dynamic range of the MPPC by more than half decade.

36. The optical engine according to claim 35, wherein the calibration factors improve linear dynamic range of the MPPC by more than one decade.

37. The optical engine according to claim 36, wherein the calibration factors improve linear dynamic range of the MPPC by more than one and one-half decade.

38. The optical engine according to claim 37, wherein the calibration factors improve linear dynamic range of the MPPC by more than two decades.

39. A flow cytometer, comprising:
a) the optical engine according to claim 30;
b) a flow cell; and
c) a pump in fluid communication with an aspiration needle for aspirating and delivering a suspension of cells through the flow cell.

40. The flow cytometer according to claim 39, further characterized in that
a) the set of lasers comprises two, three, four or five lasers, each laser tuned to a different wavelength and focused to a different vertical position along the flow cell; and
b) the set of optics spatially distinguish the filtered fluorescence in the same wavelength range that is excited by each of the two, three, four or five different lasers.

41. A flow cytometry system comprising:
c) the flow cytometer according to claim 39; and
d) a computer operably loaded with developed flow cytometry software to acquire and analyze flow cytometry data.

42. The flow cytometry system according to claim 41, wherein the software provides programming to perform the following functions:
a) acquiring data of fluorescence channels from each detector, wherein fluorescence signals collected by different detectors are converted to different data series, corresponding to the fluorescence excited by lasers at the different vertical positions;
b) generating a graphical user interface (GUI) that displays various plots for the acquired data, wherein the GUI further comprises compensation scroll bars adjacent to the comparison plots to adjust compensation of spectral overlap between one or more channel;
c) saving the acquired data into a data file.

43. A flow cytometry method comprising:
a) providing the flow cytometry system according to claim 40;
b) labeling a suspension of cells with a plurality of fluorescent labels;
c) pumping the suspension of cells through the flow channel;
d) collecting flow cytometry data; and
e) analyzing the flow cytometry data to determine the presence, absence or abundance of one or more of the plurality of fluorescent labels on or in cells of the sample.

44. The optical engine according to claim 30, wherein the altered beam is an expanded beam.

45. The optical engine according to claim 44, wherein the expanded beam comprises less than 10% variation in light intensity across its enlarged size.

46. A flow cytometer, comprising:
a) an optical engine comprising:
  i) a laser, tuned to a wavelength suited for excitation of fluorescent molecules, wherein light from the laser is focused horizontally along an x-axis to a horizontal position and vertically along a y-axis to a vertical position along an excitation plane, wherein the horizontal position along the excitation plane intersects a flow path through a flow cell of a flow cytometer;
  ii) a set of optics comprising collection optics for collecting fluorescence emitted from the flow cell and filtration optics that filter the collected fluorescence from the flow cell into different wavelength ranges, thereby providing different fluorescent channels; and
  iii) an MPPC detector at each fluorescent channel to detect fluorescence and convert light to an electrical signal;
b) a flow cell;
c) a pump in fluid communication with an aspiration needle for aspirating and delivering a suspension of cells through the flow cell; and
d) a computer operably loaded with developed flow cytometry software to acquire and analyze flow cytometry data, wherein the software comprises programming to perform the following functions:
  i) acquiring data of fluorescence channels from each detector, wherein fluorescence signals collected by different detectors are converted to different data series, corresponding to the fluorescence excited by lasers at the different vertical positions;
  ii) generating a graphical user interface (GUI) that displays various plots for the acquired data, wherein the GUI further comprises compensation scroll bars adjacent to the comparison plots to adjust compensation of spectral overlap between one or more channel; and
  iii) saving the acquired data into a data file.

* * * * *